United States Patent
Moore et al.

(10) Patent No.: US 12,337,183 B2
(45) Date of Patent: Jun. 24, 2025

(54) SYSTEMS AND METHODS FOR REDUCING NEUROSTIMULATION ELECTRODE CONFIGURATION AND PARAMETER SEARCH SPACE

(71) Applicant: Boston Scientific Neuromodulation Corporation, Valencia, CA (US)

(72) Inventors: Lisa Denise Moore, Glendale, CA (US); Mahsa Malekmohammadi, Sherman Oaks, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 556 days.

(21) Appl. No.: 17/729,456

(22) Filed: Apr. 26, 2022

(65) Prior Publication Data
US 2022/0355114 A1     Nov. 10, 2022

Related U.S. Application Data

(60) Provisional application No. 63/186,590, filed on May 10, 2021.

(51) Int. Cl.
A61N 1/36     (2006.01)
A61N 1/02     (2006.01)
A61N 1/05     (2006.01)

(52) U.S. Cl.
CPC ......... *A61N 1/36185* (2013.01); *A61N 1/025* (2013.01); *A61N 1/0551* (2013.01); *A61N 1/36135* (2013.01)

(58) Field of Classification Search
None
See application file for complete search history.

(56) References Cited

U.S. PATENT DOCUMENTS 10,076,664 B1   9/2018   Thacker et al.
10,357,657 B2   7/2019   Moffitt et al.
(Continued)

FOREIGN PATENT DOCUMENTS

WO    WO-2022240579 A1    11/2022

OTHER PUBLICATIONS

Moore, Lisa Denise, et al., "Automated Selection of Electrodes and Stimulation Parameters in a Deep Brain Stimulation System Employing Directional Leads", U.S. Appl. No. 17/649,504, filed Jan. 31, 2022.
(Continued)

*Primary Examiner* — James M Kish
*Assistant Examiner* — Sefra D. Manos
(74) *Attorney, Agent, or Firm* — Schwegman Lundberg & Woessner, P.A.

(57) ABSTRACT

Systems and methods for reducing neurostimulation electrode configuration and parameter search space and controlling electrostimulation are discussed. An exemplary system includes an implantable stimulator to provide electrostimulation via a lead comprising a plurality of electrodes, and a programming device. The programing device receives electrode position information relative to an anatomical region of interest or physiological signals respectively sensed by the plurality of electrodes, and identifies a search space of electrode configurations and parameter values for the lead with respect to the neural target. The programing device can determine a target stimulation setting based on a clinical response to electrostimulation delivered using electrodes and stimulation parameter values from the identified search space, and generate a control signal to the control the implantable stimulator to deliver electrostimulation in accordance with the target stimulation setting.

20 Claims, 12 Drawing Sheets

(56) References Cited

U.S. PATENT DOCUMENTS

| | | |
|---|---|---|
| 10,603,498 B2 | 3/2020 | Blum et al. |
| 10,716,505 B2 | 7/2020 | Blum et al. |
| 10,857,354 B2 | 12/2020 | Zhang et al. |
| 2005/0060009 A1* | 3/2005 | Goetz ............... A61N 1/36185 607/48 |
| 2008/0154340 A1* | 6/2008 | Goetz ............... A61N 1/37247 715/765 |
| 2009/0306746 A1 | 12/2009 | Blischak |
| 2015/0112403 A1* | 4/2015 | Ruffini ............... A61N 1/36025 607/45 |
| 2017/0080234 A1* | 3/2017 | Gillespie ........... A61N 1/37247 |
| 2018/0104500 A1 | 4/2018 | Blum et al. |
| 2018/0185651 A1* | 7/2018 | Astrom ............. A61N 1/36185 |
| 2019/0076645 A1 | 3/2019 | Bower et al. |
| 2019/0175915 A1 | 6/2019 | Brill et al. |
| 2019/0329047 A1 | 10/2019 | Moffitt et al. |
| 2019/0329049 A1 | 10/2019 | Carcieri et al. |
| 2020/0001091 A1 | 1/2020 | Marnfeldt |
| 2020/0376272 A1 | 12/2020 | Block et al. |
| 2021/0196956 A1 | 7/2021 | Juárez Paz |
| 2021/0330980 A1* | 10/2021 | Mueller ............... A61N 1/0529 |
| 2022/0062640 A1* | 3/2022 | Raike ................. A61N 1/36067 |

OTHER PUBLICATIONS

"European Application Serial No. 22722973.9, Response filed Jun. 17, 2024 to Communication Pursuant to Rules 161(1) and 162 EPC", 5 pgs.

"International Application Serial No. PCT/US2022/026306, International Preliminary Report on Patentability mailed Nov. 23, 2023", 7 pgs.

"International Application Serial No. PCT/US2022/026306, International Search Report mailed Aug. 8, 2022", 4 pgs.

"International Application Serial No. PCT/US2022/026306, Written Opinion mailed Aug. 8, 2022", 5 pgs.

* cited by examiner

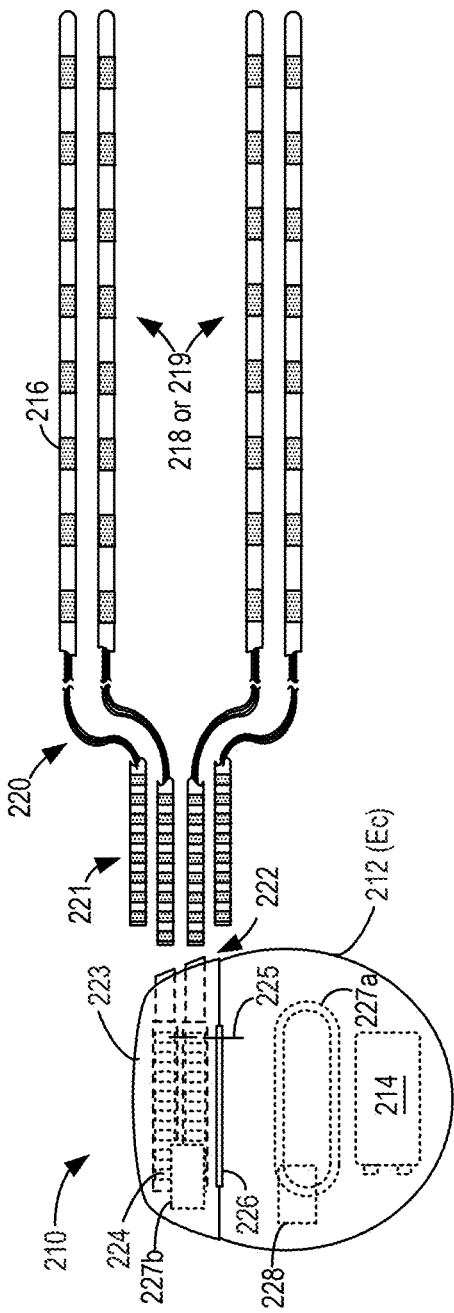
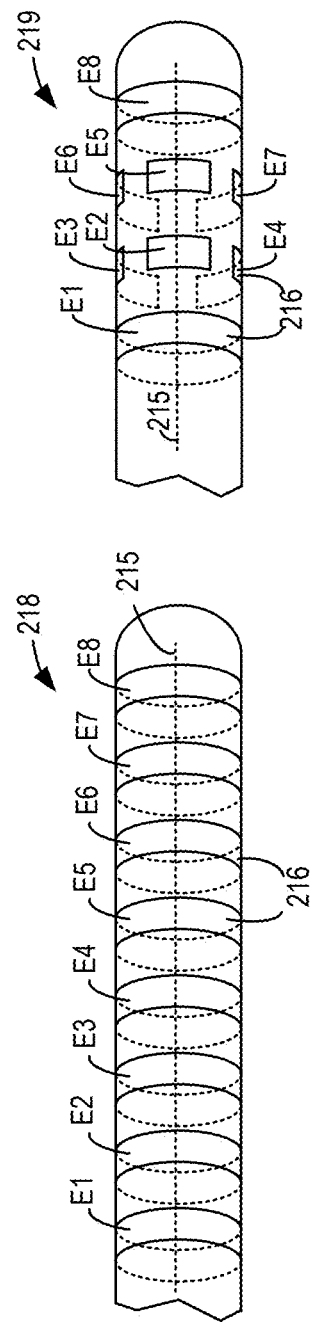
FIG. 2
FIG. 3A
FIG. 3B

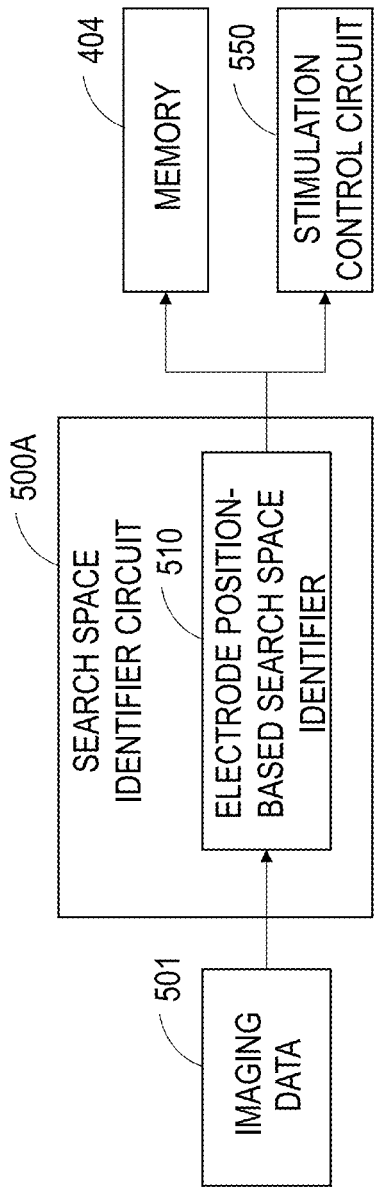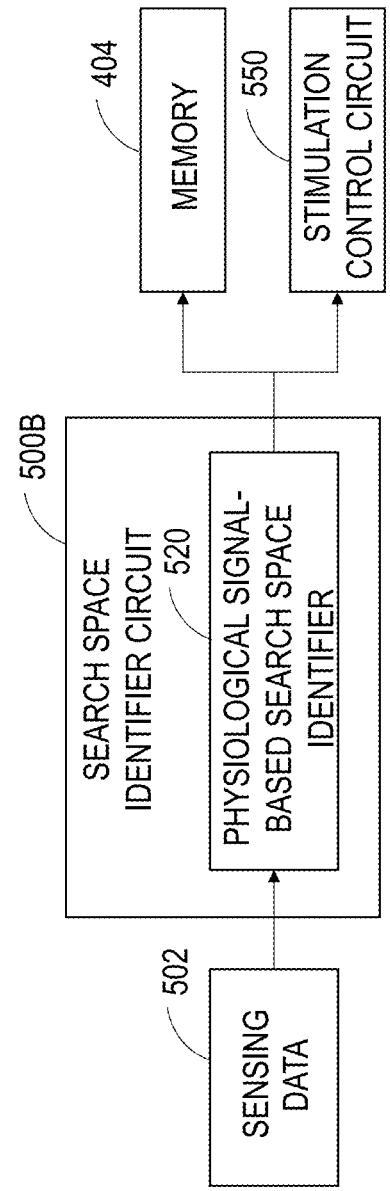
FIG. 5A
FIG. 5B

SYSTEMS AND METHODS FOR REDUCING NEUROSTIMULATION ELECTRODE CONFIGURATION AND PARAMETER SEARCH SPACE

CLAIM OF PRIORITY

This application claims the benefit of U.S. Provisional Application No. 63/186,590, filed on May 10, 2021, which is hereby incorporated by reference in its entirety.

TECHNICAL FIELD

This document relates generally to medical devices, and more particularly, to systems, devices and methods for determining and setting of stimulation parameters for programming an electrical stimulation system.

BACKGROUND

Neuromodulation (or "neural neuromodulation", also referred to as "neurostimulation" or "neural stimulation") has been proposed as a therapy for a number of conditions. Often, neuromodulation and neural stimulation may be used interchangeably to describe excitatory stimulation that causes action potentials as well as inhibitory and other effects. Examples of neuromodulation include Spinal Cord Stimulation (SCS), Deep Brain Stimulation (DBS), Peripheral Nerve Stimulation (PNS), and Functional Electrical Stimulation (FES). SCS systems have been used as a therapeutic modality for the treatment of chronic pain syndromes. PNS has been used to treat chronic pain syndrome and incontinence, with a number of other applications under investigation. FES systems have been applied to restore some functionality to paralyzed extremities in spinal cord injury patients. DBS can be used to treat a variety of diseases or disorders.

Stimulation systems, such as implantable electrostimulators, have been developed to provide therapy for a variety of treatments. An implantable electrostimulator can include a pulse generator and one or more leads each including a plurality of stimulation electrodes. The stimulation electrodes are in contact with or near target tissue to be stimulated, such as nerves, muscles, or other tissue. The control module generates a control signal to the pulse generator, which generates electrostimulation pulses that are delivered by the electrodes to the target tissue in accordance with an electrode configuration and a set of stimulation parameters.

SUMMARY

Effective neuromodulation therapy can depend on many factors including a proper selection of stimulation settings including electrode configurations (e.g., active electrodes selected for delivering stimulation energy, designation of anode and cathode) and values of one or more stimulation parameters (e.g., stimulation current amplitude, frequency, and pulse width). The possibilities of electrodes configurations and stimulation parameter values are collectively referred to as an electrode configuration and parameter search space, or simply a search space, denoted by $\Omega$. In certain neuromodulation applications such as DBS, the search space can be large due to the use of more than one lead each having multiple electrodes, along with a multitude of stimulation parameters each having a wide range of parameter values. Exploring such a large search space to look for an optimal or desired stimulation setting typically requires testing different electrode configurations and stimulation parameter combinations in multiple programming and stimulation sessions, which can be time-consuming and burdensome for the patient as well as the clinicians.

Various examples discussed in this document may provide a more efficient technique to determine an optimal or desired stimulation setting, such as by reducing the electrode configuration and parameter search space. In accordance with various examples discussed in this document, search space reduction can be achieved using spatial information of the electrodes on a lead relative to an anatomical region of interest (ROI), or physiological information collected by the electrodes at respective tissue contact locations.

The description that follows will generally focus on the use of the invention within a DBS system, such as that disclosed in U.S. Patent Application Publication 2020/0001091, which is incorporated herein by reference. However, the systems and methods discussed herein may find applicability with any implantable neurostimulator device system, including Spinal Cord Stimulation (SCS) systems, Vagus Nerve Stimulation (VNS) system, Sacral Nerve Stimulation (SNS) systems, and the like. The following examples illustrate various aspects of the examples described herein.

Example 1 is a system for providing electrostimulation to a patient, comprising: an implantable stimulator configured to provide electrostimulation to a neural target of the patient via a lead comprising a plurality of electrodes; and a programming device communicatively coupled to the implantable stimulator, the programming device including a controller configured to: receive electrode position information of the plurality of electrodes relative to an anatomical region of interest at or about the neural target, or physiological signals respectively sensed by the plurality of electrodes; identify a search space of electrode configurations and parameter values for the lead with respect to the neural target using the received electrode position information or the sensed physiological signals, the search space comprising a subset of electrodes selected from the plurality of electrodes and stimulation parameter values or value ranges associated with the subset of electrodes; determine a target stimulation setting based at least on a clinical response to electrostimulation delivered using electrodes and stimulation parameter values from the identified search space; and generate a control signal to the implantable stimulator to deliver electrostimulation in accordance with the target stimulation setting.

In Example 2, the subject matter of Example 1 optionally includes the controller that can be configured to select the subset of electrodes located within a spatial margin of the anatomical region of interest.

In Example 3, the subject matter of Example 2 optionally includes the received electrode position information that can include longitudinal positions of ring electrodes on the lead relative to the anatomical region of interest.

In Example 4, the subject matter of any one or more of Examples 2-3 optionally includes the received electrode position information that can include angular positions of segmented electrodes on the lead relative to the anatomical region of interest.

In Example 5, the subject matter of any one or more of Examples 1-4 optionally includes the controller that can be configured to determine a likelihood of an electrode being included in the identified search space based on a distance between the electrode and the anatomical region of interest.

In Example 6, the subject matter of any one or more of Examples 1-5 optionally includes the controller that can be configured to determine the stimulation parameter values or value ranges associated with an electrode based on a distance between the electrode and the anatomical region of interest.

In Example 7, the subject matter of any one or more of Examples 1-6 optionally includes the controller that can be configured to select the subset of electrodes with respective sensed physiological signals satisfying a signal strength condition or a morphological characteristic condition.

In Example 8, the subject matter of any one or more of Examples 1-7 optionally includes the physiological signals indicative of intrinsic physiological activities or evoked physiological responses to stimulation.

In Example 9, the subject matter of any one or more of Examples 1-8 optionally includes the controller that can be configured to select the subset of electrodes that (1) are located within a spatial margin of the anatomical region of interest and (2) have respective sensed physiological signals satisfying a signal strength condition or a morphological characteristic condition.

In Example 10, the subject matter of any one or more of Examples 1-9 optionally includes the plurality of electrodes that can include segmented electrodes around a circumference of the lead at a specific longitudinal position, and wherein the controller is configured to identify the search space including: identify a candidate set of the segmented electrodes that have respective sensed physiological signals satisfying a signal strength condition or morphological characteristic condition; select, from the candidate set of the segmented electrodes, a subset of segmented electrodes that are located within a spatial margin of the anatomical region of interest using the received electrode position information; and determine stimulation parameter values or value ranges for the selected subset of segmented electrodes using the received electrode position information.

In Example 11, the subject matter of any one or more of Examples 1-10 optionally includes the controller that can be configured to identify the search space including: identify, from the plurality of electrodes, a first candidate set of electrodes using the received electrode position information but without using the received physiological signals; identify, from the plurality of electrodes, a second candidate set of electrodes using the received physiological signals but without using the received electrode position information; and determine the subset of electrodes for inclusion in the search space based at least on a discrepancy metric between the first candidate set of electrodes and the second candidate set of electrodes.

In Example 12, the subject matter of Example 11 optionally includes the controller that can be configured to determine the discrepancy metric based on a distance between a spatial location of the first candidate set of electrodes and a spatial location of the second candidate set of electrodes.

In Example 13, the subject matter of any one or more of Examples 11-12 optionally includes the controller that can be configured to determine the discrepancy metric based on a distance between a center of a first stimulation field established by the first candidate set of electrodes and a center of a second stimulation field established the second candidate set of electrodes.

In Example 14, the subject matter of any one or more of Examples 11-13 optionally includes the controller that can be further configured to: determine a first reliability associated with the identified first candidate set of electrodes, and a second reliability associated with the identified second candidate set of electrodes; and in response to the discrepancy metric exceeding a threshold, select the subset of electrodes using: the first candidate set of electrodes if the first reliability exceeds a first reliability threshold and the second reliability is below a second reliability threshold; the second candidate set of electrodes if the second reliability exceeds the second reliability threshold and the first reliability is below the first reliability threshold; and a weighted combination of the first candidate set and the second candidate set of electrodes if the first reliability exceeds the first reliability threshold and the second reliability exceeds the second reliability threshold.

In Example 15, the subject matter of Example 14 optionally includes the weighted combination that can include the first candidate set and the second candidate set of electrodes scaled by respective weigh factors based on the first reliability and the second reliability.

Example 16 is a method for controlling an implantable stimulator to provide electrostimulation to a neural target of a patient via a lead comprising a plurality of electrodes. The method comprises, via a programming device: receiving electrode position information of the plurality of electrodes relative to an anatomical region of interest at or about the neural target, or physiological signals respectively sensed by the plurality of electrodes; identifying a search space of electrode configurations and parameter values for the lead with respect to the neural target using the received electrode position information or the sensed physiological signals, the search space comprising a subset of electrodes selected from the plurality of electrodes and stimulation parameter values or value ranges associated with the subset of electrodes; determining a target stimulation setting based at least on a clinical response to electrostimulation delivered using electrodes and stimulation parameter values from the identified search space; and generating a control signal to the implantable stimulator to deliver electrostimulation in accordance with the target stimulation setting.

In Example 17, the subject matter of Example 16 optionally includes identifying the parameter search spacing by selecting the subset of electrodes located within a spatial margin of the anatomical region of interest.

In Example 18, the subject matter of any one or more of Examples 16-17 optionally includes identifying the parameter search spacing by selecting the subset of electrodes having respective sensed physiological signals satisfying a signal strength condition or a morphological characteristic condition.

In Example 19, the subject matter of any one or more of Examples 16-18 optionally includes identifying the parameter search spacing by selecting the subset of electrodes that (1) are located within a spatial margin of the anatomical region of interest and (2) have respective sensed physiological signals satisfying a signal strength condition or a morphological characteristic condition.

In Example 20, the subject matter of any one or more of Examples 16-19 optionally includes the plurality of electrodes that can include segmented electrodes around a circumference of the lead at a specific longitudinal position, and wherein identifying the search space includes: identifying a candidate set of the segmented electrodes that have respective sensed physiological signals satisfying a signal strength condition or morphological characteristic condition; selecting, from the candidate set of the segmented electrodes, a subset of segmented electrodes that are located within a spatial margin of the anatomical region of interest using the received electrode position information; and determining stimulation parameter values or value ranges for the selected subset of segmented electrodes using the received electrode position information.

In Example 21, the subject matter of any one or more of Examples 16-20 optionally includes identifying the search space including: identifying, from the plurality of electrodes, a first candidate set of electrodes using the received electrode position information but without using the received physiological signals; identifying, from the plurality of electrodes, a second candidate set of electrodes using the received physiological signals but without using the received electrode position information; and determining the subset of electrodes for inclusion in the search space based at least on a discrepancy metric between the first candidate set of electrodes and the second candidate set of electrodes.

In Example 22, the subject matter of Example 21 optionally includes determining a first reliability associated with the identified first candidate set of electrodes, and a second reliability associated with the identified second candidate set of electrodes; wherein determining the subset of electrodes includes, in response to the discrepancy metric exceeding a threshold: using the first candidate set of electrodes if the first reliability exceeds a first reliability threshold and the second reliability is below a second reliability threshold; using the second candidate set of electrodes if the second reliability exceeds the second reliability threshold and the first reliability is below the first reliability threshold; or using a weighted combination of the first candidate set and the second candidate set of electrodes each scaled by respective weigh factors based on the first reliability and the second reliability if the first reliability exceeds the first reliability threshold and the second reliability exceeds the second reliability threshold.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various examples are illustrated by way of example in the figures of the accompanying drawings. Such examples are demonstrative and not intended to be exhaustive or exclusive examples of the present subject matter.

FIG. 2 illustrates, by way of example and not limitation, an implantable pulse generator (IPG) that may be used in a DBS system.

FIGS. 3A-3B illustrate, by way of example and not limitation, leads that may be coupled to an IPG to deliver electrostimulation such as DBS.

FIGS. 5A-5D illustrate, by way of example and not limitation, search space identifier circuits for determining a reduced or restricted electrode configuration and parameter search space.

DETAILED DESCRIPTION

This document describes systems and methods for reducing neurostimulation electrode configuration and parameter search space and controlling electrostimulation. According to an example, a neurostimulation system includes an implantable stimulator to provide electrostimulation via a lead comprising a plurality of electrodes, and a programming device. The programing device receives electrode position information relative to an anatomical region of interest, or physiological signals respectively sensed by the plurality of electrodes, and identifies a search space of electrode configurations and parameter values for the lead with respect to the neural target. The programming device determines a target stimulation setting based on a clinical response to electrostimulation delivered using electrodes and stimulation parameter values from the identified search space. The programming device can generate a control signal to control the implantable stimulator to deliver electrostimulation in accordance with the target stimulation setting.

Various examples described herein involve deep brain stimulation (DBS). The following detailed description of the present subject matter refers to the accompanying drawings which show, by way of illustration, specific aspects and examples in which the present subject matter may be practiced. These examples are described in sufficient detail to enable those skilled in the art to practice the present subject matter. Other examples may be utilized and structural, logical, and electrical changes may be made without departing from the scope of the present subject matter. References to "an", "one", or "various" examples in this disclosure are not necessarily to the same example, and such references contemplate more than one example. The following detailed description is, therefore, not to be taken in a limiting sense, and the scope is defined only by the appended claims, along with the full scope of legal equivalents to which such claims are entitled.

Figure 1:
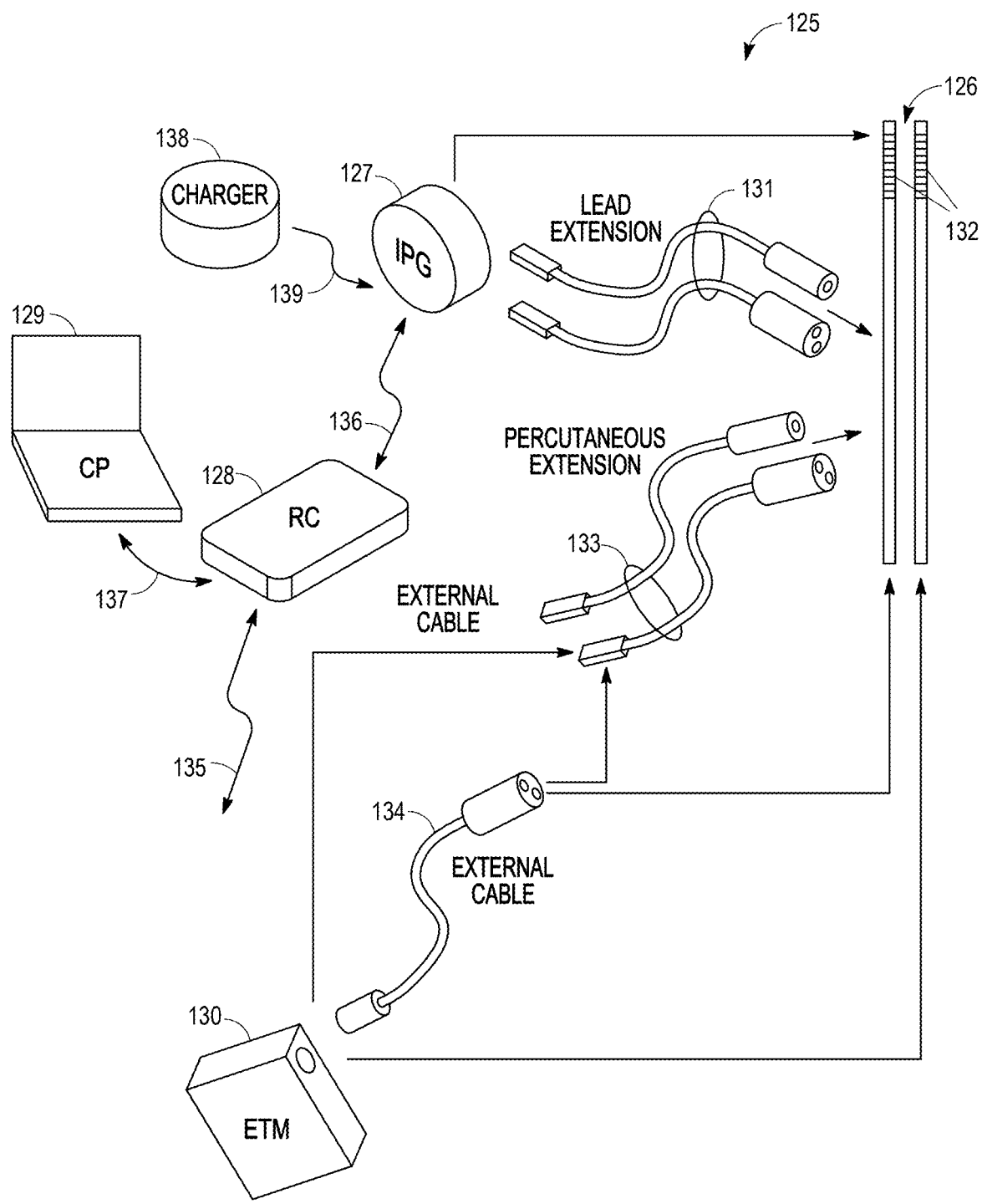
FIG. 1 illustrates, by way of example and not limitation, an electrical stimulation system that may be used to deliver deep brain stimulation (DBS).

FIG. 1 illustrates, by way of example, an example of an electrical stimulation system 100, which may be used to deliver DBS. The electrical stimulation system 100 may generally include a one or more (illustrated as two) of implantable neuromodulation leads 126, an implantable pulse generator (IPG) 127, an external remote controller (RC) 128, a clinician programmer (CP) 129, and an external trial modulator (ETM) 130. The IPG 127 may be physically connected via one or more percutaneous lead extensions 131 to the neuromodulation lead(s) 126, which carry a plurality of electrodes 132. The electrodes, when implanted in a patient, form an electrode arrangement. As illustrated, the neuromodulation leads 126 may be percutaneous leads with the electrodes arranged in-line along the neuromodulation leads or about a circumference of the neuromodulation leads. Any suitable number of neuromodulation leads can be provided, including only one, as long as the number of electrodes is greater than two (including the IPG case function as a case electrode) to allow for lateral steering of the current. Alternatively, a surgical paddle lead can be used in place of one or more of the percutaneous leads. The IPG 127 includes pulse generation circuitry that delivers electrical modulation energy in the form of a pulsed electrical waveform (i.e., a temporal series of electrical pulses) to the electrodes in accordance with a set of modulation parameters.

The ETM 130 may also be physically connected via the percutaneous lead extensions 133 and external cable 134 to the neuromodulation lead(s) 126. The ETM 130 may have similar pulse generation circuitry as the IPG 127 to deliver electrical modulation energy to the electrodes in accordance with a set of modulation parameters. The ETM 130 is a non-implantable device that may be used on a trial basis after the neuromodulation leads 126 have been implanted and prior to implantation of the IPG 127, to test the responsiveness of the modulation that is to be provided. Functions described herein with respect to the IPG 127 can likewise be performed with respect to the ETM 130.

The RC 128 may be used to telemetrically control the ETM 130 via a bi-directional RF communications link 135. The RC 128 may be used to telemetrically control the IPG 127 via a bi-directional RF communications link 136. Such control allows the IPG 127 to be turned on or off and to be programmed with different modulation parameter sets. The IPG 127 may also be operated to modify the programmed modulation parameters to actively control the characteristics of the electrical modulation energy output by the IPG 127. A clinician may use the CP 129 to program modulation parameters into the IPG 127 and ETM 130 in the operating room and in follow-up sessions.

The CP 129 may indirectly communicate with the IPG 127 or ETM 130, through the RC 128, via an IR communications link 137 or other link. The CP 129 may directly communicate with the IPG 127 or ETM 130 via an RF communications link or other link (not shown). The clinician detailed modulation parameters provided by the CP 129 may also be used to program the RC 128, so that the modulation parameters can be subsequently modified by operation of the RC 128 in a stand-alone mode (i.e., without the assistance of the CP 129). Various devices may function as the CP 129. Such devices may include portable devices such as a lap-top personal computer, mini-computer, personal digital assistant (PDA), tablets, phones, or a remote control (RC) with expanded functionality. Thus, the programming methodologies can be performed by executing software instructions contained within the CP 129. Alternatively, such programming methodologies can be performed using firmware or hardware. In any event, the CP 129 may actively control the characteristics of the electrical modulation generated by the IPG 127 to allow the desired parameters to be determined based on patient feedback or other feedback and for subsequently programming the IPG 127 with the desired modulation parameters. To allow the user to perform these functions, the CP 129 may include user input device (e.g., a mouse and a keyboard), and a programming display screen housed in a case. In addition to, or in lieu of, the mouse, other directional programming devices may be used, such as a trackball, touchpad, joystick, touch screens or directional keys included as part of the keys associated with the keyboard. An external device (e.g. CP) may be programmed to provide display screen(s) that allow the clinician to, among other functions, select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical modulation energy output by the neuromodulation leads, and select and program the IPG with modulation parameters, including electrode selection, in both a surgical setting and a clinical setting. The display screen(s) may be used to suggest the electrode(s) for use to stimulate a targeted dorsal root. The external device(s) (e.g. CP and/or RC) may be configured to communicate with other device(s), including local device(s) and/or remote device(s). For example, wired and/or wireless communication may be used to communicate between or among the devices.

An external charger 138 may be a portable device used to transcutaneously charge the IPG 127 via a wireless link such as an inductive link 136. Once the IPG 127 has been programmed, and its power source has been charged by the external charger or otherwise replenished, the IPG 127 may function as programmed without the RC 128 or CP 129 being present.

FIG. 2 illustrates, by way of example and not limitation, an IPG 210 in a DBS system. The IPG 210, which is an example of the IPG 117 of the electrical stimulation system 100 as illustrated in FIG. 1, may include a biocompatible device case 212 that holds the circuitry and a battery 214 for providing power for the IPG 210 to function, although the IPG 210 can also lack a battery and can be wirelessly powered by an external source. The IPG 210 may be coupled to one or more leads, such as leads 218 or 219 as illustrated herein. The lead 218 or 219 can each include a plurality of electrodes 216 for delivering electrostimulation energy, recording electrical signals, or both. In some examples, the leads 218 or 219 can be rotatable so that the electrodes 216 can be aligned with the target neurons after the neurons have been located such as based on the recorded signals.

The leads 218 or 219 can be implanted near or within the desired portion of the body to be stimulated. In an example of operations for DBS, access to the desired position in the brain can be accomplished by drilling a hole in the patient's skull or cranium with a cranial drill (commonly referred to as a burr), and coagulating and incising the dura mater, or brain covering. A lead can then be inserted into the cranium and brain tissue with the assistance of a stylet (not shown). The lead can be guided to the target location within the brain using, for example, a stereotactic frame and a microdrive motor system. In some examples, the microdrive motor system can be fully or partially automatic. The microdrive motor system may be configured to perform actions such as inserting, advancing, rotating, or retracing the lead.

Lead body of the leads 218 or 219 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the leads 218 or 219 may be in contact with body tissue for extended periods of time. In some examples, the leads 218 or 219 can have a cross-sectional diameter of no more than 1.5 mm and may be in the range of 0.5 to 1.5 mm.

The electrodes 216 can be made of metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use. The electrodes 216 can include one or more ring electrodes, and/or one or more sets of segmented electrodes (or any other combination of electrodes), examples of which are discussed below with reference to FIGS. 3A and 3B.

Lead wires 220 within the leads may be coupled to the electrodes 216 and to proximal contacts 221 insertable into lead connectors 222 fixed in a header 223 on the IPG 210, which header can comprise an epoxy for example. Alternatively, the proximal contacts 221 may connect to lead extensions (not shown) which are in turn inserted into the lead connectors 222. Once inserted, the proximal contacts 221 connect to header contacts 224 within the lead connectors 222, which are in turn coupled by feedthrough pins 225 through a case feedthrough 226 to stimulation circuitry 228 within the case 212, which stimulation circuitry 228 is described below.

By way of example and not limitation, the IPG 210 illustrated in FIG. 2 can be coupled to four percutaneous leads 218 or 219 (218 is shown), and thus the header 223 may include a 2×2 array of eight-electrode lead connectors 222. However, the type and number of leads, and the number of electrodes, in an IPG is application specific and therefore can vary. In another example not shown, a given lead can have sixteen electrodes, and thus this lead would have two sets of proximal contacts 221 to mate with two of the eight-electrode lead connectors 222, as disclosed for example in U.S. Patent Application Publication 2019/0076645. The conductive case 12 can also comprise an electrode (Ec).

In a DBS application, as is useful in the treatment of motor symptoms in Parkinson's disease for example, the IPG 210 is typically implanted under the patient's clavicle (collarbone). The leads 218 or 219 (which may be extended by lead extensions, not shown) can be tunneled through and under the neck and the scalp, with the electrodes 216 implanted through holes drilled in the skull and positioned for example in the subthalamic nucleus (STN) and the pedunculopontine nucleus (PPN) in each brain hemisphere. The IPG 210 can also be implanted underneath the scalp closer to the location of the electrodes' implantation. The leads 218 or 219, or the extensions 633, can be integrated with and permanently connected to the IPG 210 in other solutions.

The IPG 210 can include an antenna 227a allowing it to communicate bi-directionally with a number of external devices discussed subsequently. The antenna 227a as shown comprises a conductive coil within the case 212, although the coil of the antenna 227a can also appear in the header 223. When the antenna 227a is configured as a coil, communication with external devices preferably occurs using near-field magnetic induction. The IPG 210 may also include a Radio-Frequency (RF) antenna 227b. Although the RF antenna 227b is shown within the header 223, in some examples it may also be within the case 212. The RF antenna 227b may comprise a patch, slot, or wire, and may operate as a monopole or dipole. The RF antenna 227b preferably communicates using far-field electromagnetic waves, and may operate in accordance with any number of known RF communication standards, such as Bluetooth, Zigbee, WiFi, MICS, and the like. If the IPG 210 lacks a battery 214, an additional coil can be present to receive wireless power from an external source.

Stimulation in IPG 210 is typically provided by pulses each of which may include one phase or multiple phases. For example, a monopolar stimulation current can be delivered between a lead-based electrode (e.g., one of the electrodes 216) and the case electrode Ec 212. A bipolar stimulation current can be delivered between two lead-based electrodes (e.g., two of the electrodes 216). Stimulation parameters typically include amplitude (or voltage amplitude), frequency, pulse width of the pulses or of its individual phases; electrodes selected to provide the stimulation; polarity of such selected electrodes, i.e., whether they act as anodes that source current to the tissue, or cathodes that sink current from the tissue. Each of the electrodes can either be used (an active electrode) or unused (OFF). When the electrode is used, the electrode can be used as an anode or cathode and carry anodic or cathodic current. In some instances, an electrode might be an anode for a period of time and a cathode for a period of time. These and possibly other stimulation parameters taken together comprise a stimulation program that the stimulation circuitry 228 in the IPG 210 can execute to provide therapeutic stimulation to a patient.

In some examples, a measurement device coupled to the muscles or other tissue stimulated by the target neurons, or a unit responsive to the patient or clinician, can be coupled to the IPG 210 or microdrive motor system. The measurement device, user, or clinician can indicate a response by the target muscles or other tissue to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in, for example, tremor frequency or amplitude in response to stimulation of neurons. Alternatively, the patient or clinician can observe the muscle and provide feedback. In an example in the context of DBS, the measurement device can sense neural signals such as evoked responses from the brain, extract signal features such as morphological features indicating if the contacts from which these signals are sensed are located inside or outside the target structure in the brain.

FIGS. 3A-3B illustrate, by way of example and not limitation, leads 216 and 218 that may be coupled to the IPG 210 to deliver electrostimulation such as DBS. FIG. 3A shows a lead 218 with electrodes 216 disposed at least partially about a circumference of the lead 218. The electrodes 216 may be located along a distal end portion of the lead 218. As illustrated herein, the electrodes 216 are ring electrodes that span 360 degrees around a circumference of the lead 218. A ring electrode allows current to project equally in every direction from the position of the electrode, and typically does not enable stimulus current to be directed from only a particular angular position or a limited angular range around of the lead. The lead 218, which includes only ring electrodes, is also referred to as a non-directional lead.

FIG. 3B shows a lead 219 with electrodes 216 including ring electrodes such as E1 at a proximal end and E8 at the distal end. Additionally, the lead 219 also include a plurality of segmented electrodes (also known as split-ring electrodes). For example, a set of segmented electrodes E2, E3, and E4 are around the circumference at a longitudinal position, each spanning less than 360 degrees around the lead axis 215. In an example, each of electrodes E2, E3, and E4 spans 90 degrees, with each being separated from the others by gaps of 30 degrees. Another set of segmented electrodes E5, E6, and E7 are located around the circumference at another longitudinal position different from the segmented electrodes E2, E3 and E4. Segmented electrodes such as E2-E7 can direct stimulus current to a selected angular range around the lead.

Segmented electrodes may typically provide superior current steering than ring electrodes because target structures in DBS or other stimulation are not typically symmetric about the axis of the distal electrode array. Instead, a target may be located on one side of a plane running through the axis of the lead. Through the use of a radially segmented electrode array, current steering can be performed not only along a length of the lead but also around a circumference of the lead. This provides precise three-dimensional targeting and delivery of the current stimulus to neural target tissue, while potentially avoiding stimulation of other tissue. In some examples, segmented electrodes can be together with ring electrodes. The lead 219, which include at least one or more segmented electrodes, is also referred to as a directional lead. In an example, all electrodes on a directional lead can be segmented electrodes. In another example, there can be different numbers of segmented electrodes at different longitudinal positions.

As illustrated in FIG. 3B, segmented electrodes may be grouped into sets of segmented electrodes, where each set is disposed around a circumference of the lead 219 at a particular longitudinal portion of the directional lead 219. The directional lead 219 may have any number (e.g., three as shown in FIG. 3B) segmented electrodes in a given set of segmented electrodes. By way of example and not limitation, a given set may include any number between two to 16 segmented electrodes. In an example, all sets of segmented electrodes may contain the same number of segmented electrodes. In another example, one set of the segmented electrodes may include a different number of electrodes than at least one other set of segmented electrodes.

The segmented electrodes may vary in size and shape. In some examples, the segmented electrodes are all of the same size, shape, diameter, width or area or any combination thereof. In some examples, the segmented electrodes of each circumferential set (or even all segmented electrodes disposed on the lead 219) may be identical in size and shape.

Each set of segmented electrodes may be disposed around the circumference of the lead body to form a substantially cylindrical shape around the lead body. The spacing between individual electrodes of a given set of the segmented electrodes may be the same, or different from, the spacing between individual electrodes of another set of segmented electrodes on the lead 219. In some examples, equal spaces, gaps or cutouts are disposed between each segmented electrode around the circumference of the lead 219. In other examples, the spaces, gaps or cutouts between the segmented electrodes may differ in size or shape. In other examples, the spaces, gaps, or cutouts between segmented electrodes may be uniform for a particular set of the segmented electrodes, or for all sets of the segmented electrodes. The sets of segmented electrodes may be positioned in irregular or regular intervals along a length the lead 219.

Figure 4:
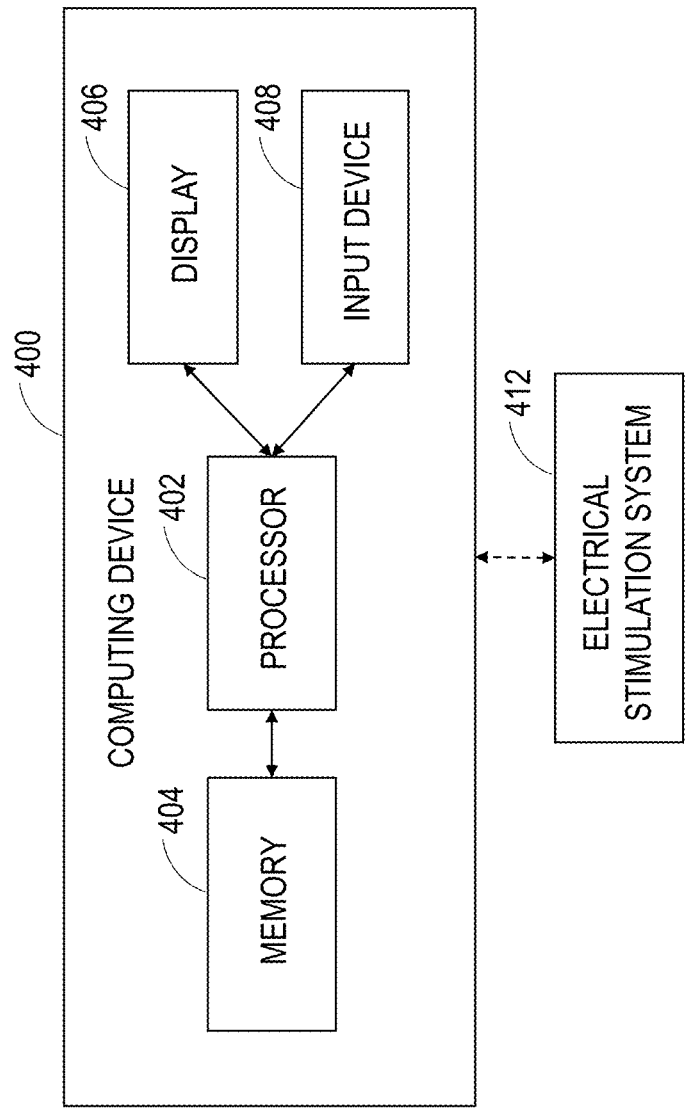
FIG. 4 illustrates, by way of example and not limitation, a computing device for programming or controlling the operation of an electrostimulation system.

FIG. 4 illustrates, by way of example and not limitation, a computing device 400 for programming or controlling the operation of an electrical stimulation system 412. The computing device 400 includes a processor 402, a memory 404, a display 406, and an input device 408. Optionally, the computing device 400 may be separate from and communicatively coupled to the electrical stimulation system 412. Alternatively, the computing device 400 may be integrated with the electrical stimulation system 412. In an example, the computing device 400 can be a part of the electrical stimulation system 412, such as part of the IPG 127, RC 128, CP 129, or ETM 130 illustrated in FIG. 1.

The computing device 400, also referred to as a programming device, can be a computer, tablet, mobile device, or any other suitable device for processing information. The computing device 400 can be local to the user or can include components that are non-local to the computer including one or both of the processor 402 or memory 404 (or portions thereof). For example, the user may operate a terminal that is connected to a non-local processor or memory. In some examples, the computing device 400 can include a watch, wristband, smartphone, or the like. Such computing devices can wirelessly communicate with the other components of the electrical stimulation system, such as the CP 129, RC 128, ETM 130, or IPG 127 illustrated in FIG. 1. The computing device 400 may be used for gathering patient information, such as general activity level or present queries or tests to the patient to identify or score pain, depression, stimulation effects or side effects, cognitive ability, or the like. In some examples, the computing device 400 may prompt the patient to take a periodic test (for example, every day) for cognitive ability to monitor, for example, Alzheimer's disease. In some examples, the computing device 400 may include or be coupled to a sensing system to sense patient clinical responses to electrostimulation such as DBS. Additionally or alternatively, the computing device 400 may receive information about patient clinical responses to electrostimulation. Based on the patient clinical responses, the computing device 400 may determine or update stimulation parameters, such as by using a closed-loop algorithm. Examples of the patient clinical responses may include physiological signals (e.g., heart rate) or motor parameters (e.g., tremor, rigidity, bradykinesia). The computing device 400 may communicate with the CP 129, RC 128, ETM 130, or IPG 127 and direct the changes to the stimulation parameters to one or more of those devices. In some examples, the computing device 400 can be a wearable device used by the patient only during programming sessions. Alternatively, the computing device 400 can be worn all of the time and continually or periodically adjust the stimulation parameters. In an example, the closed-loop algorithm for determining or updating stimulation parameters can be implemented in a mobile device, such as a smartphone, that is connected to the IPG or an evaluating device (e.g. a wristband or watch). These devices can also record and send information to the clinician.

The processor 402 can include one or more processors that may be local to the user or non-local to the user or other components of the computing device 400. In an example, the processor 402 may execute instructions (e.g., stored in the memory 404) to create or modify one or more stimulation settings selectable for use in electrostimulation therapies such as DBS. A stimulation setting includes an electrode configuration and values for one or more stimulation parameters. The electrode configuration may include information about electrodes (ring electrodes and/or segmented electrodes) selected to be active for delivering stimulation (ON) or inactive (OFF), polarity of the selected electrodes, electrode locations (e.g., longitudinal positions of ring electrodes along the length of a lead, or longitudinal positions and angular positions segmented electrodes on a circumference at a longitudinal position of the lead), stimulation modes such as monopolar pacing or bipolar pacing, etc. The stimulation parameters may include, for example, current amplitude values, current fractionalization across electrodes, stimulation frequency, stimulation pulse width, etc. The processor 402 can determine or modify a stimulation setting by searching through an electrode configuration and parameter search space Ω through an iterative optimization process, such as until an optimal, desired, or acceptable outcome is reached. The search space Ω refers to a collection of available electrodes, possible electrode configurations, and possible values or value ranges of one or more stimulation parameters that may be applied to selected electrodes to deliver electrostimulation.

One of the challenges in determining or updating a stimulation setting is that the search space Ω can be so large that the search process can be time-consuming, less effective, or burdensome for the patient as well as the clinicians. To improve search efficiency, the processor 402 can execute instructions to reduce the size of the search space Ω. In accordance with various examples discussed in this document, the search space reduction can be based on patient-specific information, such as spatial information of the electrodes relative to an anatomical region of interest (ROI) at or about the neural target (e.g., a region in a brain hemisphere), and/or physiological information collected by the electrodes at respective tissue contact locations. Examples of reducing the search space of electrode configurations and parameter values are discussed below, such as with reference to FIGS. 5A-5D.

In various examples, portions of the functions of the processor 402 may be implemented as a part of a microprocessor circuit. The microprocessor circuit can be a dedicated processor such as a digital signal processor, application specific integrated circuit (ASIC), microprocessor, or other type of processor for processing information. Alternatively, the microprocessor circuit can be a processor that can receive and execute a set of instructions for performing the functions, methods, or techniques described herein.

The memory 404 can store instructions executable by the processor 402 to perform varies functions including, for example, determining a reduced or restricted electrode configuration and parameter search space Ω* (also referred to as a restricted search space), and creating or modifying one or more stimulation settings within the restricted search space Ω*. The stimulation settings each associated with respective optimization criteria such as clinical response indicators, along with the restricted search space Ω*, may be stored in the memory 404.

The memory 404 can be a computer-readable storage media that includes, for example, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information, and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, Bluetooth™, near field communication, and other wireless media.

The display 406 can be any suitable display or presentation device, such as a monitor, screen, display, or the like, and can include a printer. The display 406 can be a part of a graphical user interface (GUI) configured to display stimulation settings (e.g., electrode configurations and stimulation parameter values and value ranges), the search space Ω, restricted search space Ω* as a result of search space reduction, among others. In some examples, the display 406 may display information provided to the processor 402 for reducing the search space and determining stimulation settings, such as a diagram illustrating electrode locations on a lead relative to the ROI at or about the neural target, and/or physiological information collected by the electrodes at respective tissue contact locations, as shown in any of FIGS. 6A-6E.

The input device 408 can be, for example, a keyboard, mouse, touch screen, track ball, joystick, voice recognition system, or any combination thereof, or the like. Another input device 408 can be a camera from which the clinician can observe the patient. Yet another input device 408 is a microphone where the patient or clinician can provide responses or queries. In some examples, the display 406 and the input device 408 can be integrated into a GUI that allows a user to provide input through one or more on-screen user interface (UI) control elements. In an example, a user may use the input device 408 to provide user input to help identify the restricted search space Ω*, such as by selecting active electrodes from a lead or defining a value range for a stimulation parameter, or confirming or modifying auto-selected active electrodes or auto-generated value range for a stimulation parameter, as described in the following with reference to FIGS. 5A-5D and 6A-6E.

The electrical stimulation system 412 can include, for example, any of the components illustrated in FIG. 1. The electrical stimulation system 412 may communicate with the computing device 400 through a wired or wireless connection or, alternatively or additionally, a user can provide information between the electrical stimulation system 412 and the computing device 400 using a computer-readable medium or by some other mechanism. As mentioned, in some examples, the computing device 400 may include part of the electrical stimulation system, such as, for example, the IPG 127, RC 128, CP 129, or ETM 130 or any combination thereof.

FIGS. 5A-5D illustrate, by way of example and not limitation, search space identifier circuits 500A-500D each configured to determine a restricted electrode configuration and parameter search space Ω* using patient-specific information. The restricted search space Ω* may include a subset of active electrodes for delivering stimulation energy, and values or ranges of values for one or more stimulation parameters for the subset of active electrodes. The search space identifier circuits 500A-500D may each be included in the processor 402. In some examples, the stimulation parameter space reduction operations taken by any of the search space identifier circuits 500A-500D may be implemented as machine-readable instructions that, when executed by a machine such as the processor 402, can produce the restricted search space Ω*.

FIG. 5A illustrates a search space identifier circuit 500A including an electrode position-based search space identifier 510 that can identify a restricted search space Ω* using electrode position information relative to an anatomical region of interest (ROI). The electrode position-based search space identifier 510 can receive imaging data 501, such as an MRI or CT scans obtained during implantation or revision of an IPG system, or during a device follow-up. The imaging data 501 may contain structural or anatomical information of a target stimulation site, and spatial locations of a plurality of electrodes with respect to neural anatomy of a ROI. In some examples, an integrated anatomy software may be applied to the imagining data 501 such as to improve image quality or to enhance feature recognition. The ROI can be determined based on lead location and the target tissue to be stimulated. In an example, the ROI can be determined in an automated process such as based on patient treatment history. For example, the ROI can include an anatomical region that has previously been stimulated and demonstrated clinical benefit with tolerable side effects. In an example, a user can manually define the ROI, such as by drawing or marking on the user interface or using other control elements.

Figure 6A:
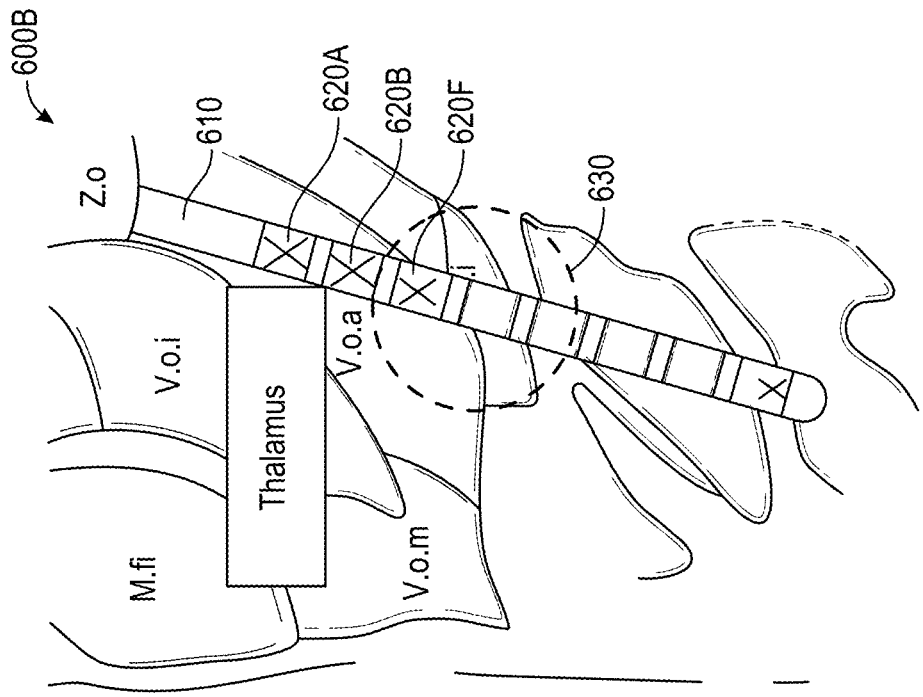
FIGS. 6A-6E illustrate, by way of example and not limitation, diagrams of electrode positions relative to an anatomy of a neural target and/or physiological signals sensed by the electrodes from respective tissue contact locations, the information of which may be used for electrode selection.

The electrode position-based search space identifier 510 can identify a subset of active electrodes located within a spatial margin of the ROI. In an example, only the identified active electrodes are included in the restricted search space $\Omega^*$. Electrodes outside the spatial margin of the ROI are excluded from the restricted search space $\Omega^*$. Referring to FIG. 6A, a diagram 600A illustrates neural anatomy of a portion of a brain (e.g., thalamus and basal ganglia) and a stimulation lead 610 placed therein to deliver electrostimulation therapy such as DBS. The diagram 600A may be displayed on the display 406. The lead 610, which is an example of the directional lead 218, comprises a plurality of ring electrodes 620A, 620B, ..., along the length of the lead 610. The ring electrodes have respective longitudinal positions on the lead 218 relative to an ROI 630. In the illustrated example, proximal electrodes 620A and 620B and distal electrode 620C are located outside the ROI 630, electrodes 620D and 620E are located within the ROI 630. Consequently, in this example, electrodes 620D and 620E are included in the restricted search space $\Omega^*$, and electrodes 620A, 620B, and 620C are excluded from the restricted search space $\Omega^*$.

The electrode position-based search space identifier 510 can similarly identify a subset of segmented electrodes in a directional lead (e.g., the directional lead 219) based on angular positions of the electrodes disposed about a circumference of a lead relative to an ROI defined on a transverse plane perpendicular to the length of the lead 610. In an example, an ROI can be a three-dimensional region including a first projection on a frontal plane parallel to the length of the lead 610, and a second projection on a transverse plane perpendicular to the length of the lead 610. Similar to the example shown in FIG. 6A where the ring electrodes have respective longitudinal positions relative to the ROI on the frontal plane, segmented electrodes disposed at respective angular positions about a circumference of a lead have respective angular positions relative to the ROI on the transverse plane perpendicular to the length of the lead. The electrode position-based search space identifier 510 can identify those segmented electrodes falling within a spatial margin of the ROI to be included in the restricted search space $\Omega^*$, and those segmented electrodes outside the spatial margin of the ROI to be excluded from the restricted search space $\Omega^*$.

The restricted search space $\Omega^*$ may also include values or value ranges for one or more stimulation parameters (e.g., stimulation current amplitude, pulse width, frequency) for the active electrodes selected to be included in the restricted search space $\Omega^*$. In an example, the stimulation parameter values or value ranges may be determined using predictions of volume of tissue that can be activated by electrostimulation based on a stimulation field model (SFM). In another example, the stimulation parameter values or value ranges may be determined based on predictions or historical measurement data of therapeutic effects and side effects of electrostimulations at the tissue sites where the selected active electrodes are located.

In some examples, the restricted search space $\Omega^*$ generated by the search space identifier circuit 500A, including the selected active electrodes and/or stimulation parameter values or value ranges, may be recommended to a user (e.g., a clinician). The user may confirm, reject, or modify the electrode selection or the stimulation parameter values or value ranges such as via the input device 408, and finalize the restricted search space $\Omega^*$.

Figure 6B:
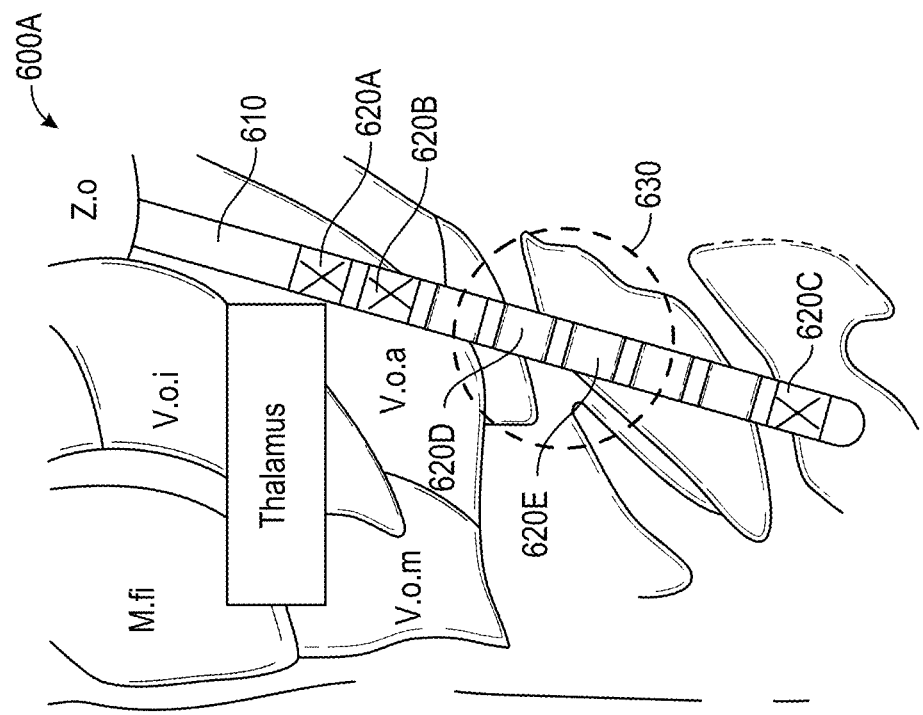

In some examples, the electrode position-based search space identifier 510 can determine a likelihood of including an electrode in the restricted search space $\Omega^*$ or a likelihood of excluding an electrode from the restricted search space $\Omega^*$. The likelihood of inclusion or exclusion can be based on a relative distance between the electrode and the ROI. Referring to FIG. 6B, a diagram 600B illustrates the neural anatomy of a portion of a brain (e.g., thalamus and basal ganglia) and the lead 610, similar to the diagram 600A of FIG. 6A. For an electrode on the lead 610, a likelihood of such electrode being identified as an active electrode and included in the restricted search space $\Omega^*$ can be inversely proportional to a distance from the electrode location to the ROI 630, such as a geometric center or other representative location of the ROI 630. Electrodes farthest away from the ROI 630, such as 620A and 620B, can be least favored to be included in $\Omega^*$. Conversely, electrodes closest to the geometric center or other representative location of the ROI 630 (such as the electrodes within the ROI 630) can be most favored to be included in $\Omega^*$. Electrodes having a middle range likelihood, such as electrode 620F, may be designated as being partially included in and partially excluded from $\Omega^*$. In an example, a partially included or a partially excluded electrode can be associated with restricted values or value range. For example, while a full range of stimulation current amplitude up to a specific maximum value of $I_{max}$ can be assigned to a first electrode with a high likelihood of inclusion, a second electrode with a lower likelihood of inclusion may be assigned with lower current amplitude or restricted amplitude range, e.g., up to X % (<100%) of $I_{max}$, where X % can be based on the likelihood of inclusion. For instance, in FIG. 6B, if the electrode 620F has a 30% likelihood of inclusion, then the current amplitude applied to the electrode 620F can be capped at approximately 30% of $I_{max}$.

Referring back to FIG. 5A, the identified restricted search space $\Omega^*$ may be stored in the memory 404. Additionally or alternatively, the restricted search space $\Omega^*$ may be provided to a stimulation control circuit 550 to determine an optimal stimulation setting or modify a previously determined optimal stimulation setting for a stimulation lead at target stimulation region, such as a region in a brain hemisphere. The stimulation control circuit 550 can be implemented as a part of the processor 402, or the CP 129 or the RC 128. As discussed previously, a stimulation setting may include an electrode configuration (e.g., active electrodes selected for delivering stimulation energy, designation of anode and cathode and stimulation mode) and values for one or more stimulation parameters (e.g., stimulation current amplitude, current fractionalization across electrodes, pulse width, and frequency). In some examples, stimulation setting optimization can be performed by a user (e.g., a clinician) during an in-clinic programming session via a graphical user interface (GUI), as discussed below with reference to FIG. 7.

In some examples, the stimulation control circuit 550 can determine or modify a stimulation setting using a feedback-control loop. For example, electrostimulation may be delivered to the patient in accordance with a stimulation setting (including a particular electrode configuration and stimulation parameter values). Feedback such as patient clinical responses indicative of therapeutic effectiveness and/or side effects of the electrostimulation may be evaluated. Based on the feedback, the stimulation control circuit 550 may explore the restricted search space $\Omega^*$ and iteratively modify the electrode configuration and/or stimulation parameter value, until an optimal, desired, or acceptable outcome is reached, such as clinical responses indicating maximal therapeutic effectiveness with minimal unwanted side effects, or until a specific stop condition is reached such as number of iterations, time spent in programming session, or the like. The resultant optimal stimulation setting, along with a unique clinical response indicator (e.g., weighted combination of clinical effects with unique weight factors) form a stimulation program that can be stored in the memory 404. Each stimulation program can be associated with, or tagged by, a unique clinical response indicator. In some examples, the stimulation control circuit 550 may use a prediction model to predict patient clinical responses to untested stimulation parameter values or untested electrode configurations in the search space, without actually delivering electrostimulation and evaluating the resultant clinical responses. The feedback-control loop for determining a stimulation setting and the model-based prediction of patient clinical responses, among other things, are described in U.S. Pat. No. 10,603,498, the entirety of which is incorporated herein by reference.

One or more stimulation programs (each including a stimulation setting associated with a unique clinical response indicator) may be stored in the memory 404. The stimulation control circuit 550 may select a stimulation program, such as based on a user input via the input device 408, and provide it to the IPG (e.g., IPG 127 or IPG 210) to deliver electrostimulation therapy in accordance with the stimulation setting of the selected stimulation program.

FIG. 5B illustrates a search space identifier circuit 500B including a physiological signal-based search space identifier 520 than can identify a restricted electrode configuration and parameter search space $\Omega^*$ using physiological information, such as sensing data 502 collected by a plurality of electrodes of a lead. The sensing data 502 may contain functional information (e.g., electrophysiologic properties of the tissue or neuroactivities of brain network) and indirect structural or anatomical information. In an example, the sensing data 502 includes physiological signals respectively sensed by the plurality of electrodes each indicative of intrinsic physiological activities or evoked physiological responses to electrostimulation. In an example, the sensing data 502 include near-field physiological signals (e.g., bioelectric signal) at respective tissue contact locations. In another example, the sensing data 502 include far-field signals, such as electrocorticography signals indicative of motor cortex activities and collected by, for example, one or more cortical paddle leads.

The physiological signal-based search space identifier 520 may identify a subset of active electrodes to be included in the restricted search space $\Omega^*$ based on a measure of signal strength or a morphological characteristic of the sensed signal. Referring to FIG. 6C, a diagram 600C illustrates the lead 610 similar to the diagram 600A of FIG. 6A. The electrodes 620A, 620B, etc. on the lead 610, which are used for delivering electrostimulation, may also sense respective physiological signals 640A, 640B, etc. In the illustrated example, the physiological signals are local bioelectric signals sensed at respective tissue contact locations. The physiological signals may be sensed using a monopolar configuration, or a bipolar configuration. As illustrated, proximal electrodes 620A and 620B and distal electrode 620C sense no or weak signals physiological signals 640A, 640B, and 640C, respectively; in contrast, electrodes 620D and 620E each sense stronger physiological signals 640D and 640E, respectively. In an example, the physiological signal-based search space identifier 520 may compare the signal strength (e.g., amplitude, signal power, or other signal metrics) to a threshold, and identify electrodes 620D and 620E as active electrodes to be included in the restricted search space $\Omega^*$ on the basis of the corresponding physiological signals each exceeding a threshold, and exclude electrodes 620A, 620B, and 620C from the restricted search space $\Omega^*$ on the basis that the corresponding physiological signals each falling below the threshold. Alternatively, the physiological signal-based search space identifier 520 may compare the morphology of the sensed physiological signal to a template morphology of a known physiological response, and identify active electrodes to be included in the restricted search space $\Omega^*$ based on a similarity metric between the morphology of the sensed physiological signal to the template morphology (e.g., the similarity metric exceeding a threshold).

In some examples, the physiological signal-based search space identifier 520 may determine, for an electrode, a likelihood of inclusion or a partial inclusion in the restricted search space $\Omega^*$, such as based on the signal strength or the signal morphological similarity to the template morphology. A partially included electrode may have a restricted stimulation parameter value or value range, as similarly discussed above with reference to FIG. 6A.

The restricted search space $\Omega^*$ identified by physiological signal-based search space identifier 520 may be stored in the memory 404, and/or provided to the stimulation control circuit 550 to determine an optimal stimulation setting or modify a previously determined optimal stimulation setting for a stimulation lead at target stimulation region, as similarly discussed above with reference to FIG. 5A.

Figure 5C:
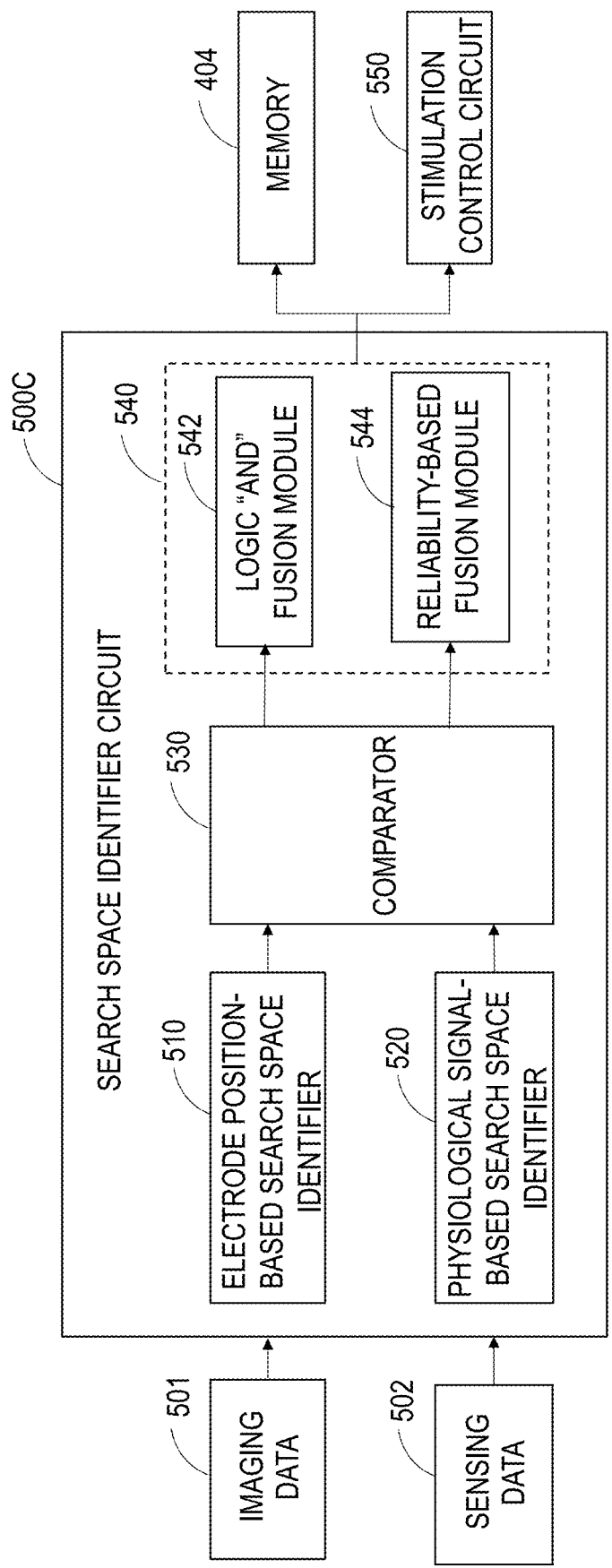

In some examples, both the electrode position information and the physiological information sensed from multiple electrodes at their respective tissue contact locations may be used to identify active electrodes to be included in the restricted search space $\Omega^*$. FIG. 5C illustrates a search space identifier circuit 500C including the electrode position-based search space identifier 510, the physiological signal-based search space identifier 520, a comparator 530, and a fusion module 540. The lead position-based search space identifier 510 can identify a first candidate search space $\Omega_E$ using only the electrode position information without using sensed physiological information from the electrodes. The physiological signal-based search space identifier 520 can identify a second candidate search space $\Omega_S$ using only the sensed physiological information without using the electrode position information. The comparator 530 can compare the first candidate search space $\Omega_E$ to the second candidate search space $\Omega_S$, and determine if $\Omega_E$ is in agreement with $\Omega_S$, or an amount of discrepancy or disagreement between the two candidate search spaces $\Omega_S$ and $\Omega_E$. The disagreement between $\Omega_S$ and $\Omega_E$ may be attributed to different information source used by the respective search space reduction algorithms. For example, the imaging data 501 contain primarily structural and anatomical information relative to the electrode and lead placement, and the sensing data 502 contains primarily functional information such as electrophysiologic properties of the tissue and neuroactivities of brain network. Additionally or alternatively, the disagreement may be a result of uncertainties associated with the search space reduction algorithms employed by the electrode position-based search space identifier 510 and the signal-based search space identifier 520. For example, interferences and noises introduced to the imaging data 501 during acquisition and inherent error in the image analysis workflow or missing data may affect the performance of electrode position-based search space identifier 510, and reduce the reliability of the resultant candidate search space $\Omega_E$. On the other hand, sensing data 502 quality may also be affected by noise or uncertainties of intraoperative timing, missing data and the performance of the signal-based search space identifier 520 may also be affected by the lesion effect, brain tissue shift and/or lead rotation during implant compared to final lead position.

In an example, the comparator 530 may determine a discrepancy metric between the candidate search spaces $\Omega_E$ and $\Omega_S$ based on a distance between a represented location (e.g., a geometric center) of the candidate subset of electrodes in $\Omega_E$ and a representative location (e.g., a geometric center) of the candidate subset of electrodes in $\Omega_S$. In another example, the discrepancy metric can be determined based on a distance between a center of a first stimulation field established by the candidate subset of electrodes in $\Omega_E$ and a center of a second stimulation field established the candidate subset of electrodes in $\Omega_S$. The stimulation field may be estimated using a stimulation field model (SFM).

The fusion module 540 may apply a fusion algorithm to $\Omega_E$ and $\Omega_S$ and determine the restricted search space $\Omega^*$. In an example, the fusion module 540 includes a logic "AND" fusion module 542 that determines the restricted search space $\Omega^*$ as an intersection between candidate search spaces $\Omega_E$ and $\Omega_S$. For example, only those electrodes that are located within a spatial margin of a specific ROI and have corresponding sensed physiological signals satisfying a signal strength or morphological characteristic condition are recognized as active electrodes to be included in the restricted search space $\Omega^*$.

In another example, the fusion module 540 includes a reliability-based fusion module 544 that determines the restricted search space $\Omega^*$ using one or both of the candidate search spaces $\Omega_E$ or $\Omega_S$, if the comparator 530 indicates a disagreement between $\Omega_E$ or $\Omega_S$, such as the discrepancy metric exceeding a discrepancy threshold. The disagreement between $\Omega_E$ or $\Omega_S$ may be represented by different subsets of active electrodes being selected from the same lead. The reliability-based fusion module 544 may select one of $\Omega_E$ or $\Omega_S$ as the restricted search space $\Omega^*$, or use a combination of $\Omega_E$ and $\Omega_S$ to determine the restricted search space $\Omega^*$, depending upon reliabilities associated with the respective candidate search spaces. In an example, the reliability-based fusion module 544 can determine a first reliability factor $R_E$ indicative of a confidence of lead position-based search space reduction and the resultant candidate search space $\Omega_E$, including confidence of electrode positions relative to the ROI. The first reliability factor $R_E$ can be determined using information about brain tissue shift, quality of imaging data 501, lead positions orientation detection, subcortical segmentation, among others. The reliability-based fusion module 544 can determine a second reliability factor $R_S$ indicative of a confidence of physiological signal-based search space reduction and the resultant candidate search space $\Omega_S$, including confidence of the physiological information sensed by electrodes at respective tissue contacts. The second reliability factor $R_S$ can be determined using information including changes in patient symptoms due to lesion or stun effect, change in the lead orientation due to unwanted rotation, or signal quality, data loss, etc.

The reliability-based fusion module 544 can determine the restricted search space $\Omega^*$ using the lead position-based candidate search space $\Omega_E$ if the first reliability factor $R_E$ exceeds a first reliability threshold ($R_{Eth}$) and the second reliability factor $R_S$ is below a second reliability threshold ($R_{Sth}$). The reliability-based fusion module 544 can determine the restricted search space $\Omega^*$ using the physiological signal-based candidate search space $\Omega_S$ if the second reliability factor $R_S$ exceeds the second reliability threshold and the first reliability factor $R_E$ is below the first reliability threshold. If the first reliability factor $R_E$ exceeds the first reliability threshold, and the second reliability factor $R_S$ exceeds the second reliability threshold, then the reliability-based fusion module 544 can determine the restricted search space $\Omega^*$ using a combination of the lead position-based candidate search space $\Omega_E$ and the physiological signal-based candidate search space $\Omega_S$. In an example, the combination is a weighted combination of $\Omega_E$ and $\Omega_S$ each scaled by respective weight factors $w_E$ and $w_S$. The restricted search space $\Omega^*$ as determined by the reliability-based fusion module 544 can be summarized in Equation (1) below:

$$\Omega^* = \begin{cases} \Omega_E & \text{If } R_E > R_{Eth} \text{ and } R_S < R_{Sth} \\ \Omega_S & \text{If } R_S > R_{Sth} \text{ and } R_E < R_{Eth} \\ w_E \Omega_E + w_S \Omega_S & \text{If } R_E > R_{Eth} \text{ and } R_S > R_{Sth} \end{cases} \quad (1)$$

In an example, the weight factors $w_E$ and $w_S$ can be determined based on the respective reliability factors $R_E$ and $R_S$. A larger reliability factor indicates a higher confidence for the search space; consequently, a larger weight can be assigned to that search space. In an example, the weight factors $w_E$ and $w_S$ can each be proportional to the respective reliability factors $R_E$ and $R_S$. In an example, the weight factors can be determined using Equation (2) below:

$$w_E = \frac{R_E}{R_E + R_S}; w_S = \frac{R_S}{R_E + R_S} \quad (2)$$

In an example where identifying the restricted search space $\Omega^*$ includes identifying a subset of active electrodes for providing electrostimulation, the electrode position-based search space identifier 510 can identify a first candidate set of electrodes (as part of $\Omega_E$) using the received electrode position information but without using the received physiological signals. The physiological signal-based search space identifier 520 can identify a second candidate set of electrodes (as part of $\Omega_S$) using the received physiological signals but without using the received electrode position information. The reliability-based fusion module 544 can determine the subset of active electrodes using Equations (1) and (2) above.

Figure 6D:
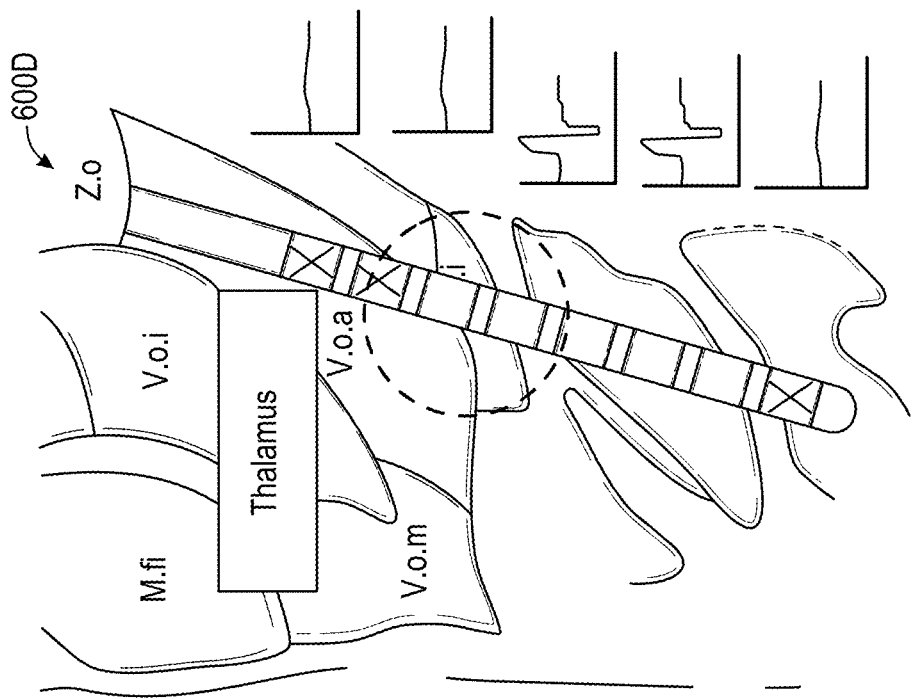
Figure 6C:
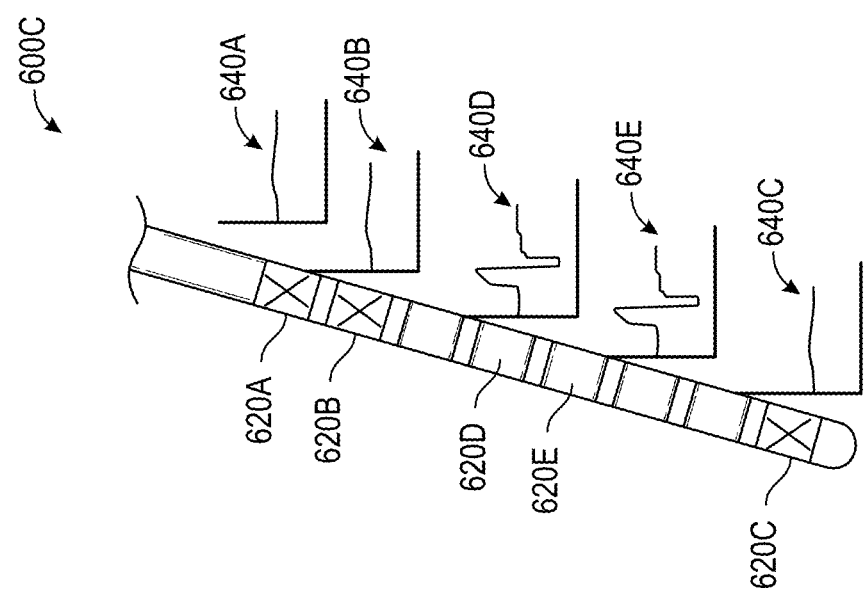

Referring to FIG. 6D, a diagram 600D illustrates neural anatomy of a portion of a brain (e.g., thalamus and basal ganglia) and the stimulation lead 610 as similarly shown in FIG. 6A, as well as physiological signals sensed by the electrodes at respective tissue contact locations as similarly shown in FIG. 6C. The diagram 600D may be displayed on the display 406 to show an agreement or disagreement between the electrode position-based electrode selection and the physiological signal-based electrode selection. As discussed above, the user may use the input device 408 to provide user input for selecting active electrodes, or confirming or modifying the active electrodes selected by the search space identifier circuit 500C and recommended to the user.

Figure 6E:
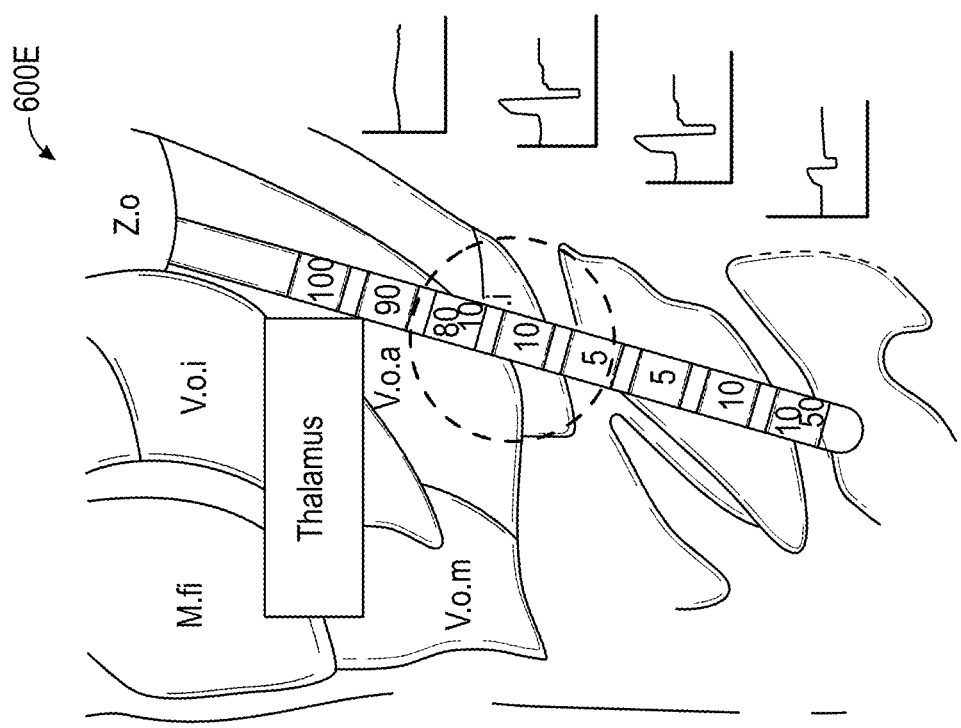

In FIG. 6E, a diagram 600E illustrates the neural anatomy of a portion of a brain (e.g., thalamus and basal ganglia) and the lead 610 similar to the diagram 600A of FIG. 6A. For each electrode on the lead 610, a value or a range of values of a stimulation parameter (e.g., stimulation current amplitude, current fractionalization, pulse width, frequency) for the electrode can be inversely proportional to a distance measured from the electrode location to the ROI 630. For example, electrodes farthest away from the ROI may be assigned with lowest current amplitudes or current fractionalization compared to electrodes closer to the ROI. As illustrated in FIG. 6E, each electrode is given a penalty score. A higher penalty score (e.g., 90 or 100) indicates a lower current amplitude or a smaller fractionized current that may be assigned to the electrode. Conversely, a lower penalty score (e.g., 10 or 5) indicates a higher current amplitude or a larger fractionized current that may be assigned to the electrode. Additionally or alternatively, an electrode with a higher penalty score has a lower priority being tested by the stimulation control circuit 550 to determine an optimal stimulation setting. Conversely, an electrode with a lower penalty score has a higher priority being tested to determine an optimal stimulation setting.

Figure 5D:
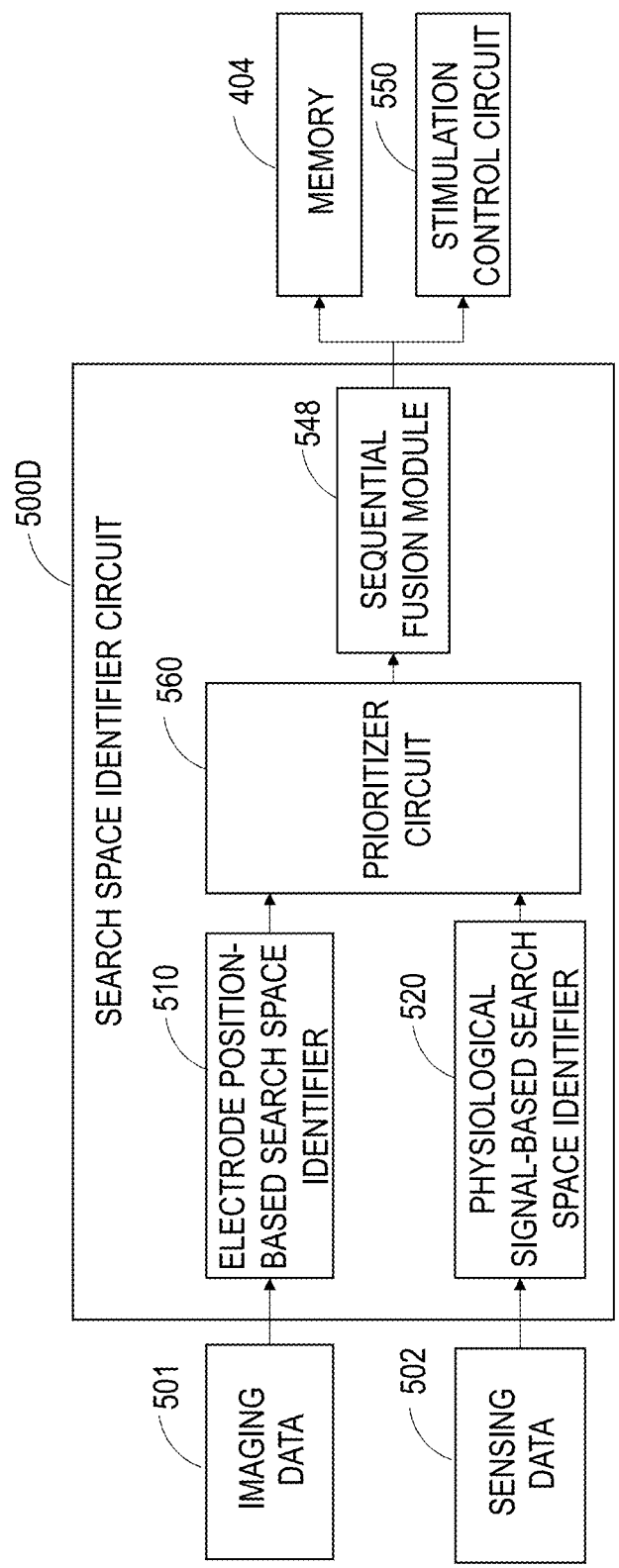

FIG. 5D illustrates another example of search space identifier circuit 500D that can identify a restricted search space $\Omega^*$ using a fusion of different search space reduction approaches such as provided by the electrode position-based search space identifier 510 and the physiological signal-based search space identifier 520. Instead of identifying candidate electrode configuration and parameter search spaces $\Omega_E$ and $\Omega_S$ independently from the original search space $\Omega$ using respectively the electrode position information and the sensed physiological information as described above in FIG. 5C, the search space identifier circuit 500D can determine the restricted search space $\Omega^*$ through sequential application of the position-based search space identifier 510 and the physiological signal-based search space identifier 520. The parameter space identifier circuit 500D includes a prioritizer circuit 560 that can prioritize one search space identifier (e.g., the identifier 510 or the identifier 520) over the other search space identifier (e.g., the identifier 520 or the identifier 510). The identifier with a higher priority is referred to as a primary identifier. The identifier with a lower priority is referred to as a secondary identifier. The sequential fusion module 548 may apply the primary identifier to generate an initial estimate of $\Omega^*$, and then apply the secondary identifier to confirm or modify the initial estimate of $\Omega^*$.

Prioritization can be based on, for example, sufficient collective analysis of the use of active electrodes in the search space and associated outcome. In an example of prioritizing electrode configurations, those shared by the position-based search space identifier 510 and the physiological signal-based search space identifier 520 can be preferentially searched, while those more strongly associated with either the position-based search space identifier 510 or the physiological signal-based search space identifier 520, but not shared by both identifiers, may receive less search priority.

In an example of excluding segmented electrodes (or angular positions of the segmented electrodes) on a directional lead such as the lead 219, the sequential fusion module 548 may use the physiological signal-based search space identifier 520 as the primary identifier, determine an initial subset of the segmented electrodes $\{E\}_S$ with the corresponding sensed physiological signals satisfying a signal strength or morphological characteristic condition. The sequential fusion module 548 may then apply the position-based search space identifier 510 as a secondary check to confirm or modify the identified electrode subset $\{E\}_S$, or further select from $\{E\}_S$ a subset of active electrodes $\{E\}_{SE}$ located within a spatial margin of a specific ROI, with the expectation that segmented electrodes excluded based on electrode locations will not be the same as the segmented electrodes (and the tissue contacts) excluded based on sensed physiological information. The resultant sequentially selected active electrodes $\{E\}_{SE}$ may be included in the restricted search space $\Omega^*$. Because the secondary check is performed on a reduced parameter space (the candidate search space obtained from the primary search space reduction) rather than on the original search space $\Omega$, the overall search time can be reduced.

In another example of excluding from the restricted search space $\Omega^*$ certain values or value ranges for a stimulation parameter such as current amplitudes across electrodes, the sequential fusion module 548 may use the position-based search space identifier 510 as the primary identifier to determine an initial estimate of values or value ranges of current amplitude $\{I\}_E$ based on the distances of the electrodes to the ROI 630, as discussed above with reference to FIG. 6E. The sequential fusion module 548 may then use the physiological signal-based search space identifier 520 as a secondary check of the values or value ranges of current amplitude $\{I\}_E$, or to further refine the values or value ranges of current amplitude based on the physiological signals sensed at respective electrode locations. The resultant sequentially selected active electrodes $\{I\}_{ES}$ may be included in the restricted search space $\Omega^*$.

Figure 7:
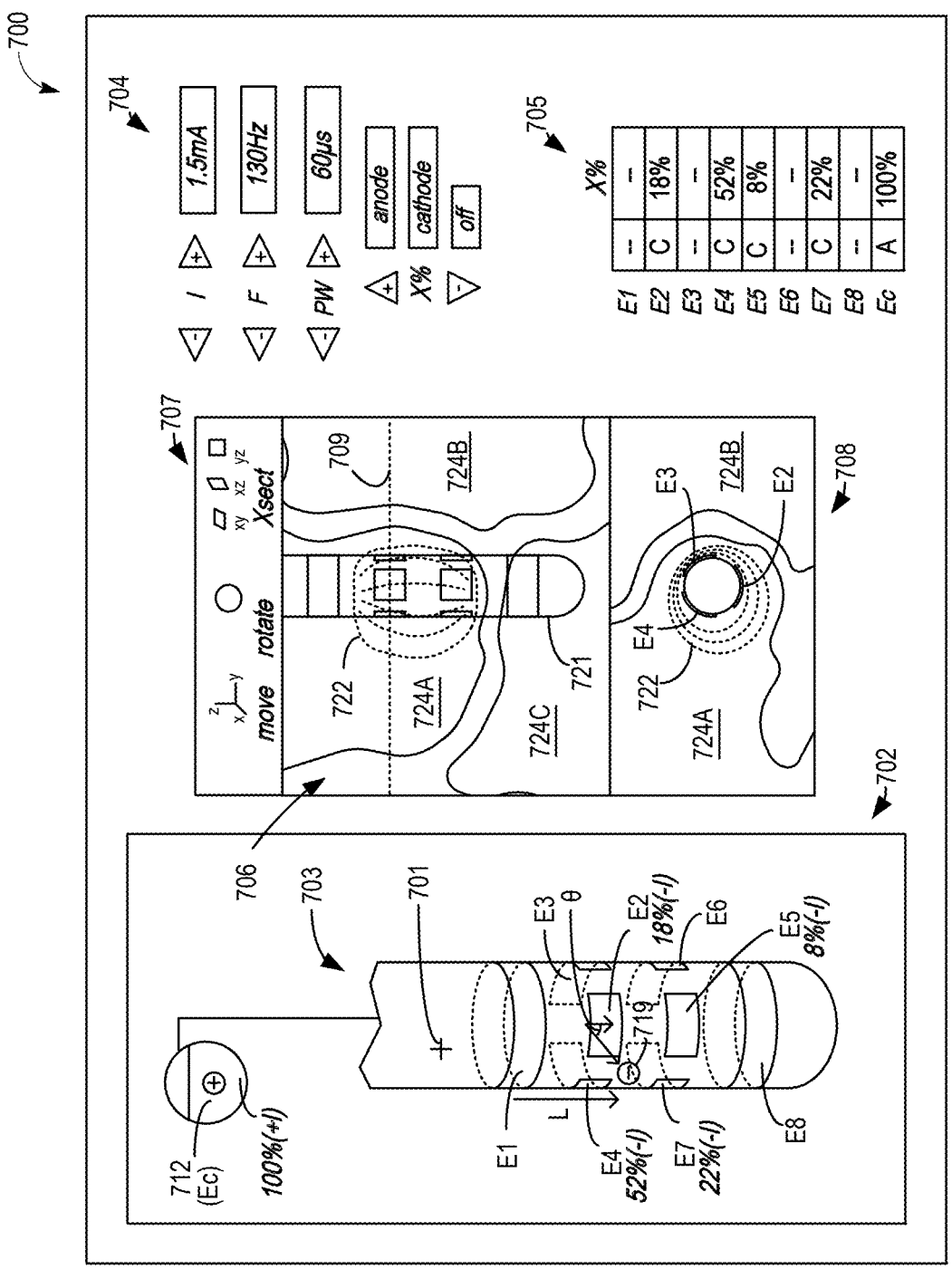
FIG. 7 illustrates, by way of example and not limitation, a graphical user interface (GUI) for programming a stimulation setting into an IPG.

FIG. 7 illustrates, by way of example and not limitation, a graphical user interface (GUI) 700 operable on an external device such as the clinician program (CP) 129, which allows a user (e.g., a clinician) to program a stimulation setting into the IPG (e.g., IPG 127 or IPG 210). The GUI 700 can be rendered on a display of the CP 129, and provide a clinician with a visual indication of how a stimulation setting (e.g., electrode configuration and/or values for a plurality of stimulation parameters) may interact with target tissue (e.g., brain tissue in the context of DBS) in which the electrodes are implanted. The GUI 700 may be used during surgical implantation of the leads 218 or 219 and the IPG 210, but may also be used after implantation to assist in creating, modifying, or selecting a therapeutically useful stimulation setting for the patient.

The GUI 700 can be controlled by a cursor 701 that the user can move using a tracking device such as a mouse connected to the CP 129. The GUI 700 may include a stimulation waveform interface 704 that allows a user to select, and adjust a value of, a stimulation waveform parameter, such as a stimulation amplitude (e.g., a current I), a frequency (F), or a pulse width (PW) of stimulation pulses. The value adjustment can be within a range as defined in a restricted search space $\Omega^*$ such as generated by one of the search space identifier circuits 500A, 500B, 500C, or 500D, as described above. In some examples, the waveform interface 704 can be significantly more complicated, particularly if the IPG 210 supports the provision of stimulation that is more complicated than a repeating sequence of pulses. In some examples, the waveform interface 704 may allow a user to select biphasic or monophasic pulses, and to select whether passive charge recovery will be used (not shown).

The GUI 700 may include an electrode configuration interface 705 which allows the user to select and modify a particular electrode configuration, such as specifying which electrodes are active electrodes (ON) to provide stimulation, and which electrodes are inactive electrodes (OFF) to refrain from providing stimulation. For an active electrode, the user may also use the electrode configuration interface 705 to specific polarity and relative magnitude for that active electrode. Electrode configurations such as selection of active electrodes, along with current adjustment (or adjustment of other stimulation parameters) for the active electrodes, can be made within the restricted search space $\Omega^*$ such as generated by one of the search space identifier circuits 500A, 500B, 500C, or 500D, as described above. As illustrated in FIG. 7, the user may use the electrode configuration interface 705 to designate an electrode as an anode (A), a cathode (C), or an inactive electrode (OFF), and to specific an amount of the total anodic or cathodic current +I or −I (specified in the waveform interface 704) that a selected active electrode will receive in a form of fraction or percentage (X %) of the total current provided. Such a split of the current among multiple electrodes is referred to as current fractionalization. In an example as illustrated in FIG. 7, the case electrode 212 Ec is specified as the only anode that receives 100% of anodic current +I. The corresponding cathodic current −I is split among a set of selected active cathode electrodes including E2 (18% of −I), E4 (52% of −I), E5 (8% of −I), and E7 (22% of −I). Two or more electrodes can be chosen to act as anodes or cathodes at a given time, allowing the electric field in the tissue to be shaped. Once the stimulation waveform interface 704 and electrode configuration interface 705 are determined, they can be sent to the IPG 210, which can produce stimulation pulses accordingly, and deliver the stimulation pulses to the patient.

The GUI 700 can include a leads interface 702 showing an image 703 of the lead being used for the patient. By way of example and not limitation, the lead shown in the image 703 includes two ring electrodes E1 and E8, a first group of segmented electrodes E2-E4 on a circumference of a first longitudinal position of the lead, and a second group of segmented electrodes E5-E7 on a circumference of a second longitudinal position of the lead. In this example, segmented electrodes E2, E4, E5, and E7 are selected as cathodes to receive fractionalized current. Such current fractionalization sets a particular position for a cathode pole 719 in a three-dimensional space. The position of this cathode pole 719 can be quantified at a particular longitudinal position L along the lead (e.g., relative to a point on the lead such as the longitudinal position of electrode E1). If a directional lead such as lead 219 is uses, the position of the cathode pole 719 may further be quantified at a particular rotational angle θ (e.g., relative to a particular angle on the lead such as relative to the center of electrode E2). The position (L, θ) of the cathode pole 719, as shown in the leads interface 702, may be virtual; that is, the position may not necessarily be at a physical position of any electrode on the lead, but a point in the three-dimensional space of the leads interface 702. In some examples, the interface 702 can include a selection to access a library of images 703 of the types of leads (e.g., 218 or 219) that may be implanted in different patients, which may be stored with the CP 129. The cursor 701 can be used to select an electrode such as any of E1-E8, or the case electrode Ec, or a pole such as cathode pole 719. As described above, electrode selection and configuration of the electrodes can be made within the restricted search space $\Omega^*$.

The CP 129 can include and execute an electrode configuration algorithm to determine a position of the cathode pole 719 in the three-dimensional space from a given electrode configuration, or determine an electrode configuration from a given position of the cathode pole 719. For example, the user can place the position of the cathode pole 719 using the cursor 701. The electrode configuration algorithm can then be used to compute an electrode configuration (e.g., current fractionalization across a plurality of selected active electrodes) that best places the cathode pole 719 in this position. The electrode configuration algorithm may thus calculate that electrode E4 should receive the largest share of cathodic current (52%*−I), while E2, E7, and E6 which are farther away from the cathode pole 719 receive lesser percentages, as shown in the stimulation parameters interface 704. By involving more than one electrode, cathode pole 719 is formed as a virtual pole not as the position of any of the physical electrodes. Again, the electrode configuration algorithm can also operate in reverse: from a given electrode configuration, the position of the cathode pole 719 can be determined. The electrode configuration algorithm is described further in U.S. Patent Application Publication 2019/0175915, which is incorporated herein by reference.

The GUI 700 can further include a visualization interface 706 that allows a user to view a stimulation field image 722 formed on a lead given the selected stimulation parameters and electrode configuration. The stimulation field image 722 is formed by field modelling in the CP 129. The visualization interface 706 may include tissue imaging information, such as imaging information of different brain tissue structures 724A, 724B and 724C in the context of DBS. Such tissue imaging information may come from a Magnetic Resonance Image (MRI) or Computed Tomography (CT) image of the patient, may come from a generic library of images, and may include user defined regions. The GUI 700 can overlay the lead image 721 and the stimulation field image 722 with the tissue imaging information in the visualization interface 706 so that the position of the stimulation field image 722 relative to the various tissue structures 724A-624C can be visualized. The various images shown in the visualization interface 706 (i.e., the lead image 721, the stimulation field image 722, and the tissue structures 724A-624C) can be three-dimensional in nature, and hence may be rendered to allow such three-dimensionality to be better appreciated by the user, such as by shading or coloring the images, etc. A view adjustment interface 707 may allow the user to use the cursor 701 to move or rotate the images. As illustrated in FIG. 7, a cross-section interface 708 allows the various images to be seen in a particular two-dimensional cross section, such as a cross section 709 taken perpendicularly to the lead image 721 and through the segmented electrodes E2, E3, and E4.

The GUI 700 can be particularly useful because it allows the electric field as reflected in stimulation field image 722 to be seen relative to surrounding tissue structures 724A-624C. This allows the user to adjust the stimulation parameters to recruit, or avoid recruiting, particular tissue structures. Assume for example that it is desirable for a given patient to stimulate tissue structure 724A, but to not stimulate tissue structures 724B or 724C where the stimulation may cause undesired side effects. The clinician can then use the GUI 700 to adjust stimulation (e.g., to adjust the stimulation parameters or the electrode configuration) to move the stimulation field (e.g., the cathode pole 719) to a proper position (L, θ). In the example shown, and as best seen in the cross-section interface 708, higher cathodic currents are provided at electrodes E4 (52%*–I) and E2 (18%*–I), because these electrodes are generally facing towards tissue structure 724A where stimulation is ideally applied. By contrast, electrode E3 carries no cathodic current because it generally faces towards tissue structure 724B where stimulation is ideally avoided. The result is a stimulation field that is more predominant in tissue structure 724A and less predominant in tissue structure 724B, as shown in the visualization interface 706.

Especially in a DBS application, it is important that correct stimulation parameters be determined for a given patient. Improper stimulation parameters may not yield effective relief of a patient's symptoms, or may cause unwanted side effects. To determine proper stimulation, a clinician may use the GUI 700 to try different combinations of stimulation parameters and electrode configurations. This may occur, during a DBS patient's surgery when the leads are being implanted, or during a post-surgery office visit after the patient has had a chance to heal and after the position of the leads stabilize in the patient.

Figure 8:
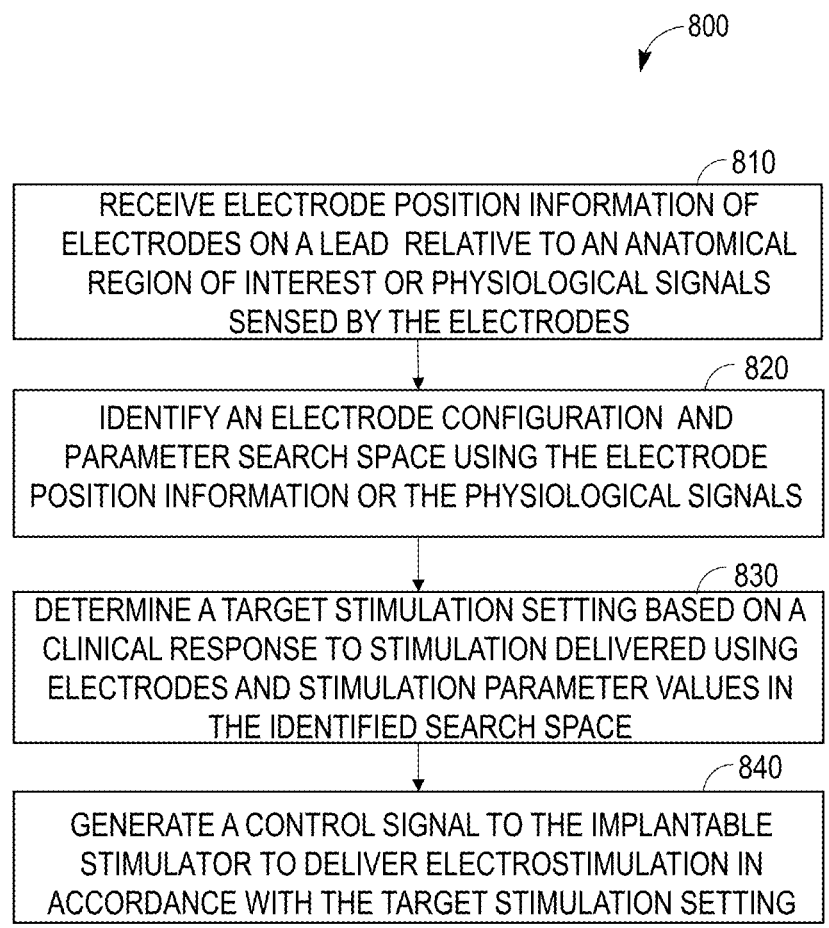
FIG. 8 is a flow chart illustrating, by way of example and not limitation, a method for identifying a reduced electrode configuration and parameter search space and providing electrostimulation to a neural target.

FIG. 8 is a flow chart illustrating, by way of example and not limitation, a method 800 for identifying a reduced electrode configuration and parameter search space and providing electrostimulation to a neural target, such as DBS to brain tissue. The method 800 may be carried out using a medical system, such as the electrical stimulation system 100 in FIG. 1 or the electrical stimulation system 412 in FIG. 4. The electrostimulation may be generated by an implantable stimulator such as the IPG 127 or the IPG 210, and delivered to the neural target via a lead comprising a plurality of electrodes, such as the ring electrodes on the non-directional lead 218 or the segmented electrodes on the directional lead 219. Portions of the method 800 may be implemented in an external device, such as the CP 129 or the RC 128 in FIG. 1 or the computing device 400 in FIG. 4, which can identify an electrode configuration and parameter search space, and search for a target stimulation setting within the identified search space that may be used by an implantable stimulator to provide electrostimulation to the patient.

At 810, electrode position information of the electrodes on the lead relative to an anatomical region of interest (ROI) at or about the neural target can be received by a programming device, such as the computing device 400. The electrode position information can be obtained from images such as an MRI or CT scans. Such images contain structural or anatomical information of the neural target, and spatial locations of the electrodes with respect to the neural anatomy at the ROI. An example image of a portion of a brain (e.g., thalamus and basal ganglia) and a stimulation lead with electrodes at respective locations relative an ROI is shown FIG. 6A. The ROI can be determined automatically based on lead location and the target tissue to be stimulated, based on patient treatment history, or specified by a user via the input device 408.

Additionally or alternatively, physiological signals respectively sensed by the electrodes at their respective tissue contact locations may be received by the programming device at 810. The physiological signals contain functional information (e.g., electrophysiologic properties of the tissue or neuroactivities of brain network) and indirect structural or anatomical information. The physiological signals can represent intrinsic physiological activities, or evoked responses to electrostimulation. The physiological signals can be near-field physiological signals at respective tissue contact locations, or far-field signals such as those representing motor cortex activities. Example physiological signals sensed by electrodes at respective contact locations are shown in FIG. 6C.

At 820, an electrode configuration and parameter search space (also referred to as a search space) for the lead with respect to the neural target may be identified using the received electrode position information or the sensed physiological signals. The search space thus identified is a reduced or restricted search space comprising a subset of electrodes selected from the plurality of electrodes on the lead, and stimulation parameter values or value ranges associated with the selected subset of electrodes. Identification of such search space can be carried out using any of the search space identifier circuits 500A-500D, as discussed above with reference to FIGS. 5A-5D. An example of identifying the restricted search space $\Omega^*$ using the electrode position information relative to the ROI is illustrated in FIG. 6A. Only those electrodes located within a spatial margin of the ROI can be include in the restricted search space $\Omega^*$. Electrodes outside the spatial margin of the ROI are excluded from the restricted search space $\Omega^*$. The electrode position-based search space identifier may select ring electrodes and segmented electrodes using respective ROIs, or different projections of an ROI such as on planes parallel or perpendicular to the lead. In some examples, an electrode may be "partially" included in the restricted search space $\Omega^*$. A likelihood of including or excluding an electrode may be determined based on a relative distance between the electrode and the ROI. A partially included electrode may have a restricted stimulation parameter value or value range.

In an example, the restricted search space $\Omega^*$ can be identified using the physiological signals sensed by the electrodes of a lead at respective tissue contact locations, as illustrated in FIG. 6C. A physiological signal-based search space identifier may determine whether to include an electrode in the restricted search space $\Omega^*$ based on the signal strength (e.g., amplitude, signal power, or other signal metrics) or a morphological characteristic of the physiological signal sensed by that electrode. For example, electrodes associated with physiological signals having signal strengths exceeding a threshold can be included in restricted search space $\Omega^*$, while electrodes with physiological signals having signal strengths falling below the threshold can be excluded from $\Omega^*$. Alternatively, electrodes associated with physiological signals morphologically similar to a template morphology of a known physiological response can be included in $\Omega^*$, while electrodes associated with physiological signals morphologically dissimilar to the template morphology can be excluded from $\Omega^*$. In an example, for an electrode, the likelihood of inclusion or the partial inclusion in the restricted search space $\Omega^*$ may be determined based on the signal strength or the signal morphological similarity to the template morphology.

In an example, the restricted search space $\Omega^*$ can be identified using both the electrode position information and the physiological information sensed from multiple electrodes at their respective tissue contact locations. Candidate search spaces $\Omega_E$ or $\Omega_S$ can be determined based on the electrode position information and the physiological signals, respectively. The search space $\Omega_E$ includes electrodes that are located within a spatial margin of a specific ROI. The search space spaces $\Omega_S$ includes electrodes with the sensed physiological signals satisfying a signal strength or morphological characteristic condition. The restricted search space $\Omega^*$ may be determined using an intersection between $\Omega_E$ and $\Omega_S$, such as by using the logic "AND" fusion module 542 in FIG. 5C. Only those electrodes that are located within a spatial margin of a specific ROI, and have corresponding sensed physiological signals satisfying a signal strength or morphological characteristic condition, are recognized as active electrodes to be included in the restricted search space $\Omega^*$. Alternatively, the restricted search space $\Omega^*$ may be selected as either one of $\Omega_E$ or $\Omega_S$, or a combination of $\Omega_E$ and $\Omega_S$, depending upon reliabilities associated with the respective candidate search spaces, such as by using the reliability-based fusion module 544 in FIG. 5C. For example, if the reliabilities associated with both candidate search spaces $\Omega_E$ or $\Omega_S$ are both high (e.g., exceeding respective reliability thresholds), then the electrodes (or the locations thereof) to be included in the restricted search space $\Omega^*$ can be determined using a weighted combination of the first candidate set of electrodes in $\Omega_E$ and the second candidate set of electrodes in $\Omega_S$ each scaled by respective weigh factors based on the first reliability and the second reliability. In yet another example, the restricted search space $\Omega^*$ can be identified using a sequential application of the position-based search space identifier and the physiological signal-based search space identifier, as illustrated in FIG. 5D. One of the position-based search space identifier or the physiological signal-based search space identifier is recognized as a primary identifier and the other recognized as secondary identifier. The primary identifier identifiers an initial subset of the electrodes, and the secondary identifier performs a secondary check to confirm or modify the initial electrode subset.

At 830, a target stimulation setting may be determined based at least on a clinical response to electrostimulation delivered using electrodes and stimulation parameter values in the identified search space $\Omega^*$, such as using the stimulation control circuit 550. The determination of the target stimulation setting may involve a feedback-control loop, where the electrode configuration and/or stimulation parameter value can be iteratively adjusted within the restricted search space $\Omega^*$, until an optimal, desired, or acceptable outcome is reached, such as clinical responses indicating maximal therapeutic effectiveness with minimal unwanted side effects, or until a specific stop condition is reached such as number of iterations, time spent in programming session, or the like. In some examples, a prediction model trained using machine learning algorithms may be used to predict patient clinical responses to untested stimulation parameter values or untested electrode configurations in the restricted search space $\Omega^*$. The target stimulation setting can be stored in a memory.

At 840, a control signal can be generated to control the implantable stimulator to deliver electrostimulation in accordance with target stimulation setting. In some examples, multiple stimulation settings may be stored in a memory. In response to a control signal, a stimulation setting can be selected and provided to the IPG to deliver electrostimulation therapy.

Figure 9:
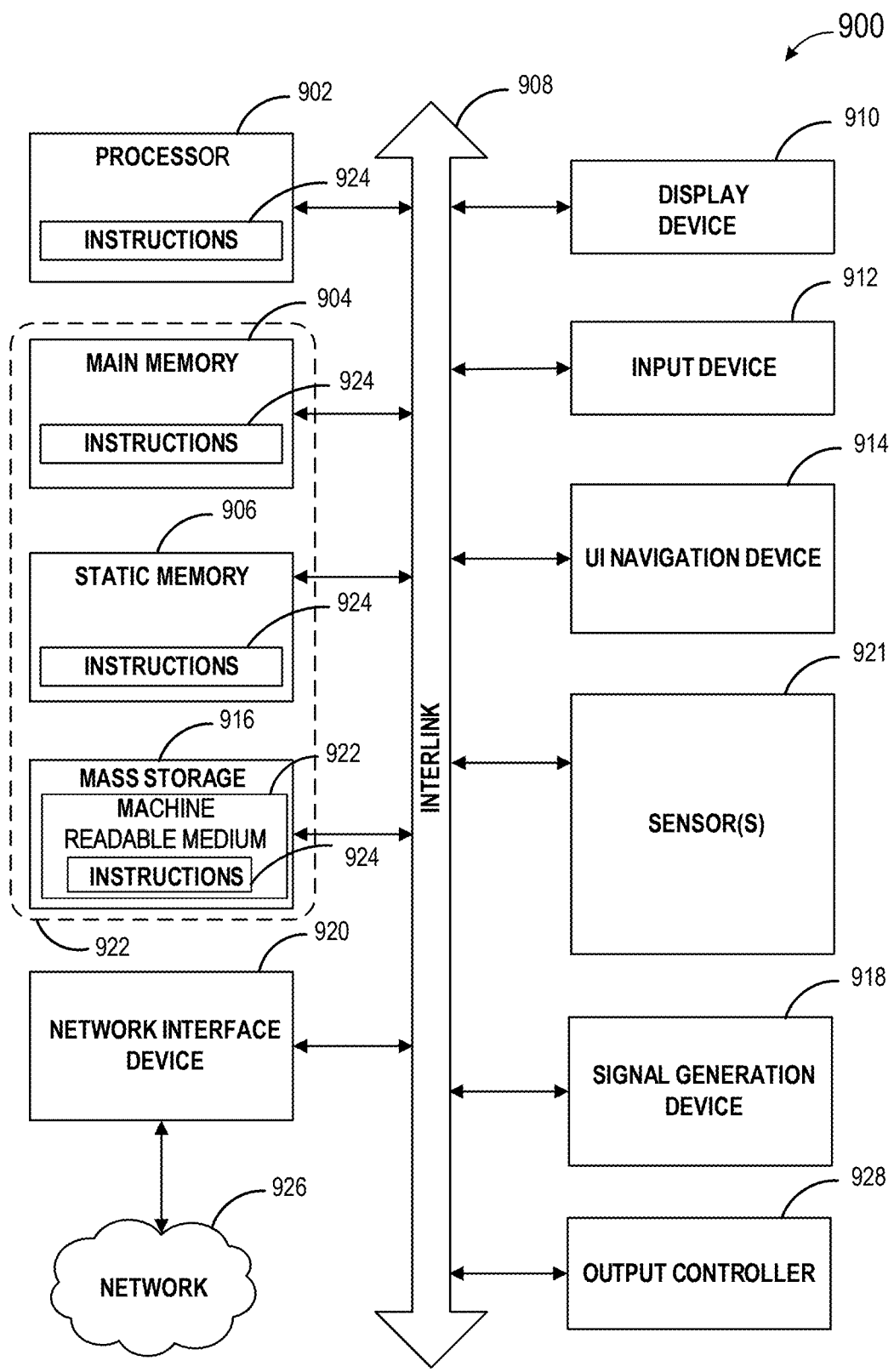
FIG. 9 illustrates generally a block diagram of an example machine 900 upon which any one or more of the techniques (e.g., methodologies) discussed herein may perform.

FIG. 9 illustrates generally a block diagram of an example machine 900 upon which any one or more of the techniques (e.g., methodologies) discussed herein may perform. Portions of this description may apply to the computing framework of various portions of the neuromodulation device or the external programming device.

In alternative examples, the machine 900 may operate as a standalone device or may be connected (e.g., networked) to other machines. In a networked deployment, the machine 900 may operate in the capacity of a server machine, a client machine, or both in server-client network environments. In an example, the machine 900 may act as a peer machine in peer-to-peer (P2P) (or other distributed) network environment. The machine 900 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), among other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions for the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 900 may include a hardware processor 902 (e.g., a central processing unit (CPU), a graphics processing unit (GPU), a hardware processor core, algorithm specific ASIC, or any combination thereof), a main memory 904 and a static memory 906, some or all of which may communicate with each other via an interlink (e.g., bus) 908. The machine 900 may further include a display unit 910 (e.g., a raster display, vector display, holographic display, etc.), an alphanumeric input device 912 (e.g., a keyboard), and a user interface (UI) navigation device 914 (e.g., a mouse). In an example, the display unit 910, input device 912 and UI navigation device 914 may be a touch screen display. The machine 900 may additionally include a storage device (e.g., drive unit) 916, a signal generation device 918 (e.g., a speaker), a network interface device 920, and one or more sensors 921, such as a global positioning system (GPS) sensor, compass, accelerometer, or other sensors. The machine 900 may include an output controller 928, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 916 may include a machine readable medium 922 on which is stored one or more sets of data structures or instructions 924 (e.g., software) embodying or utilized by any one or more of the techniques or functions described herein. The instructions 924 may also reside, completely or at least partially, within the main memory 904, within static memory 906, or within the hardware processor 902 during execution thereof by the machine 900. In an example, one or any combination of the hardware processor 902, the main memory 904, the static memory 906, or the storage device 916 may constitute machine readable media.

While the machine-readable medium 922 is illustrated as a single medium, the term "machine readable medium" may include a single medium or multiple media (e.g., a centralized or distributed database, and/or associated caches and servers) configured to store the one or more instructions 924.

The term "machine readable medium" may include any medium that is capable of storing, encoding, or carrying instructions for execution by the machine 900 and that cause the machine 900 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 924 may further be transmitted or received over a communication network 926 using a transmission medium via the network interface device 920 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 920 may include one or more physical jacks (e.g., Ethernet, coaxial, or phone jacks) or one or more antennas to connect to the communication network 926. In an example, the network interface device 920 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 900, and includes digital or analog communications signals or other intangible medium to facilitate communication of such software.

Various examples are illustrated in the figures above. One or more features from one or more of these examples may be combined to form other examples.

The method examples described herein may be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code may form portions of computer program products. Further, the code may be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for providing electrostimulation to a patient, comprising:
   an implantable stimulator configured to provide electrostimulation to a neural target of the patient via a lead comprising a plurality of electrodes; and
   a programming device communicatively coupled to the implantable stimulator, the programming device including a controller configured to:
   receive electrode position information of the plurality of electrodes relative to an anatomical region of interest at or about the neural target, or physiological signals respectively sensed by the plurality of electrodes;
   identify a search space of electrode configurations and parameter values for the lead with respect to the neural target using the received electrode position information and the sensed physiological signals, the search space comprising a subset of electrodes selected from the plurality of electrodes and stimulation parameter values or value ranges associated with the subset of electrodes;
   determine a target stimulation setting based at least on a clinical response to electrostimulation delivered using electrodes and stimulation parameter values from the identified search space; and
   generate a control signal to the implantable stimulator and cause delivery of electrostimulation to the patient in accordance with the determined target stimulation setting,
   wherein to identify the search space, the controller is configured to:
   identify, from the plurality of electrodes, a first candidate set of electrodes using the received electrode position information but without using the received physiological signals;
   identify, from the plurality of electrodes, a second candidate set of electrodes using the received physiological signals but without using the received electrode position information; and determine the subset of electrodes for inclusion in the search space based at least on a discrepancy metric between the first candidate set of electrodes and the second candidate set of electrodes.

2. The system of claim 1, wherein the controller is configured to identify the first candidate set of electrodes located within a spatial margin of the anatomical region of interest.

3. The system of claim 2, wherein the received electrode position information includes longitudinal positions of one or more ring electrodes or angular positions of segmented electrodes on the lead.

4. The system of claim 1, wherein the controller is configured to determine a likelihood of an electrode being included in the first candidate set based on a distance between the electrode and the anatomical region of interest.

5. The system of claim 1, wherein the controller is configured to determine stimulation parameter values or value ranges associated with an electrode based on a distance between the electrode and the anatomical region of interest.

6. The system of claim 1, wherein the controller is configured to identify the second candidate set of electrodes with respective sensed physiological signals satisfying a signal strength condition or a morphological characteristic condition.

7. The system of claim 1, wherein the controller is configured to select the subset of electrodes that (1) are located within a spatial margin of the anatomical region of interest and (2) have respective sensed physiological signals satisfying a signal strength condition or a morphological characteristic condition.

8. The system of claim 1, wherein the plurality of electrodes include segmented electrodes around a circumference of the lead at a specific longitudinal position, and wherein the controller is configured to identify the search space including:
   identify a candidate set of the segmented electrodes that have respective sensed physiological signals satisfying a signal strength condition or morphological characteristic condition;
   select, from the candidate set of the segmented electrodes, a subset of segmented electrodes that are located within a spatial margin of the anatomical region of interest using the received electrode position information; and
   determine stimulation parameter values or value ranges for the selected subset of segmented electrodes using the received electrode position information.

9. The system of claim 1, wherein the controller is configured to determine the discrepancy metric based on a distance between a spatial location of the first candidate set of electrodes and a spatial location of the second candidate set of electrodes.

10. The system of claim 1, wherein the controller is configured to determine the discrepancy metric based on a distance between a center of a first stimulation field established by the first candidate set of electrodes and a center of a second stimulation field established the second candidate set of electrodes.

11. The system of claim 1, wherein the controller is further configured to:
   determine a first reliability associated with the identified first candidate set of electrodes, and a second reliability associated with the identified second candidate set of electrodes; and
   in response to the discrepancy metric exceeding a threshold, select the subset of electrodes using:
   the first candidate set of electrodes if the first reliability exceeds a first reliability threshold and the second reliability is below a second reliability threshold;
   the second candidate set of electrodes if the second reliability exceeds the second reliability threshold and the first reliability is below the first reliability threshold; and
   a weighted combination of the first candidate set and the second candidate set of electrodes if the first reliability exceeds the first reliability threshold and the second reliability exceeds the second reliability threshold.

12. The system of claim 11, wherein the weighted combination includes the first candidate set and the second candidate set of electrodes scaled by respective weigh factors based on the first reliability and the second reliability.

13. The system of claim 1, wherein the controller is configured to determine the subset of electrodes for inclusion in the search space by applying a fusion algorithm to the first and the second candidate sets of electrodes based at least in part on the discrepancy metric.

14. A method for controlling an implantable stimulator to provide electrostimulation to a neural target of a patient via a lead comprising a plurality of electrodes, the method comprising, via a programming device:
   receiving electrode position information of the plurality of electrodes relative to an anatomical region of interest at or about the neural target, or physiological signals respectively sensed by the plurality of electrodes;
   identifying a search space of electrode configurations and parameter values for the lead with respect to the neural target using the received electrode position information and the sensed physiological signals, the search space comprising a subset of electrodes selected from the plurality of electrodes and stimulation parameter values or value ranges associated with the subset of electrodes;
   determining a target stimulation setting based at least on a clinical response to electrostimulation delivered using electrodes and stimulation parameter values from the identified search space; and
   generating a control signal to the implantable stimulator and causing delivery of electrostimulation to the patient in accordance with the determined target stimulation setting,
   wherein identifying the search space includes:
      identifying, from the plurality of electrodes, a first candidate set of electrodes using the received electrode position information but without using the received physiological signals;
      identifying, from the plurality of electrodes, a second candidate set of electrodes using the received physiological signals but without using the received electrode position information; and
      determining the subset of electrodes for inclusion in the search space based at least on a discrepancy metric between the first candidate set of electrodes and the second candidate set of electrodes.

15. The method of claim 14, wherein identifying the parameter search spacing includes identifying the first candidate set of electrodes located within a spatial margin of the anatomical region of interest.

16. The method of claim 14, wherein identifying the parameter search spacing includes identifying the second candidate set of electrodes having respective sensed physiological signals satisfying a signal strength condition or a morphological characteristic condition.

17. The method of claim 14, wherein identifying the parameter search spacing includes selecting the subset of electrodes that (1) are located within a spatial margin of the anatomical region of interest and (2) have respective sensed physiological signals satisfying a signal strength condition or a morphological characteristic condition.

18. The method of claim 14, wherein the plurality of electrodes include segmented electrodes around a circumference of the lead at a specific longitudinal position, and wherein identifying the search space includes:
  identifying a candidate set of the segmented electrodes that have respective sensed physiological signals satisfying a signal strength condition or morphological characteristic condition;
  selecting, from the candidate set of the segmented electrodes, a subset of segmented electrodes that are located within a spatial margin of the anatomical region of interest using the received electrode position information; and
  determining stimulation parameter values or value ranges for the selected subset of segmented electrodes using the received electrode position information.

19. The method of claim 14, further comprising determining a first reliability associated with the identified first candidate set of electrodes, and a second reliability associated with the identified second candidate set of electrodes; wherein determining the subset of electrodes includes, in response to the discrepancy metric exceeding a threshold:
  using the first candidate set of electrodes if the first reliability exceeds a first reliability threshold and the second reliability is below a second reliability threshold;
  using the second candidate set of electrodes if the second reliability exceeds the second reliability threshold and the first reliability is below the first reliability threshold; or
  using a weighted combination of the first candidate set and the second candidate set of electrodes each scaled by respective weigh factors based on the first reliability and the second reliability if the first reliability exceeds the first reliability threshold and the second reliability exceeds the second reliability threshold.

20. The method of claim 14, wherein determining the subset of electrodes for inclusion in the search space includes applying a fusion algorithm to the first and the second candidate sets of electrodes based at least in part on the discrepancy metric.

* * * * *